US008335606B2

(12) United States Patent
Mian et al.

(10) Patent No.: US 8,335,606 B2
(45) Date of Patent: Dec. 18, 2012

(54) THERMAL IMAGING-BASED VEHICLE ANALYSIS

(75) Inventors: Zahid F. Mian, Loudonville, NY (US); Jeremy C. Mullaney, Troy, NY (US); Nicholas Glasser, Wynantskill, NY (US)

(73) Assignee: International Electronic Machines Corporation, Troy, NY (US)

( * ) Notice: Subject to any disclaimer, the term of this patent is extended or adjusted under 35 U.S.C. 154(b) by 474 days.

(21) Appl. No.: 12/603,958

(22) Filed: Oct. 22, 2009

(65) Prior Publication Data
US 2010/0100275 A1 Apr. 22, 2010

Related U.S. Application Data

(60) Provisional application No. 61/193,012, filed on Oct. 22, 2008.

(51) Int. Cl.
*G01M 17/00* (2006.01)
*G06F 11/30* (2006.01)
*H01L 31/00* (2006.01)

(52) U.S. Cl. ........ 701/29.1; 250/330; 701/19; 701/29.2; 701/117

(58) Field of Classification Search ............... 250/316.1, 250/330–334, 338.1; 701/19, 29.1–29.3, 701/29.6, 31.4, 31.6, 32.7, 32.8, 33.4, 33.7, 701/34.3, 34.4, 117
See application file for complete search history.

(56) References Cited

U.S. PATENT DOCUMENTS

| | | | |
|---|---|---|---|
| 2,999,151 A | 9/1961 | Rosett | |
| 3,206,596 A | 9/1965 | Howell | |
| 3,596,519 A | 8/1971 | Blonder et al. | |
| 3,767,146 A | 10/1973 | Gallagher | |
| 3,812,343 A | 5/1974 | Gallagher et al. | |
| 4,068,811 A | 1/1978 | Caulier | |
| 4,313,583 A | 2/1982 | Bambara et al. | |
| 4,608,599 A * | 8/1986 | Kaneko et al. ............... | 348/164 |
| 4,659,043 A | 4/1987 | Gallagher | |
| 4,679,068 A * | 7/1987 | Lillquist et al. ............... | 348/33 |

(Continued)

FOREIGN PATENT DOCUMENTS
JP 2005351705 A 12/2005

OTHER PUBLICATIONS

Jonathan M. Dager, "Final Office Action", U.S. Appl. No. 11/748,714, 24 pages.

(Continued)

*Primary Examiner* — Paul N Dickson
*Assistant Examiner* — Laura Freedman
(74) *Attorney, Agent, or Firm* — John W. LaBatt; Hoffman Warnick LLC

(57) ABSTRACT

Analysis of a vehicle is performed using multi-dimensional infrared image data acquired for the vehicle. A component of the vehicle can be identified within the infrared image data, and the infrared image data for the component can be analyzed to determine whether any condition(s) are present on the vehicle. One or more actions can be initiated in response to a determination that a particular condition is present. Additionally, visible image data can be used to supplement the infrared image data. Still further, infrared image data for similar components imaged concurrently with the component can be used to identify whether any condition(s) are present on the vehicle. Unlike prior art approaches in the rail industry, the analysis can be performed on rail vehicles within a classification yard.

20 Claims, 15 Drawing Sheets

U.S. PATENT DOCUMENTS

| | | | |
|---|---|---|---|
| 4,751,571 A * | 6/1988 | Lillquist | 348/164 |
| 4,820,057 A | 4/1989 | Berndt | |
| 4,878,761 A | 11/1989 | Duhrkoop | |
| 4,977,586 A | 12/1990 | Curry | |
| 5,060,890 A | 10/1991 | Utterback et al. | |
| 5,100,243 A | 3/1992 | Grosskopf et al. | |
| 5,133,605 A | 7/1992 | Nakamura | |
| 5,201,483 A | 4/1993 | Sutnar et al. | |
| 5,331,311 A | 7/1994 | Doctor | |
| 5,381,700 A | 1/1995 | Grosskopf, Jr. | |
| 5,397,900 A | 3/1995 | Wetzler | |
| 5,448,072 A | 9/1995 | Gallagher | |
| 5,478,151 A | 12/1995 | Duhrkoop | |
| 5,583,765 A | 12/1996 | Kleehammer | |
| 5,636,026 A | 6/1997 | Mian et al. | |
| 5,660,470 A | 8/1997 | Mench | |
| 5,677,533 A | 10/1997 | Yaktine et al. | |
| 5,730,526 A | 3/1998 | Davis et al. | |
| 5,743,645 A | 4/1998 | Jaynes | |
| 5,936,737 A * | 8/1999 | Naumann | 356/613 |
| 5,942,753 A | 8/1999 | Dell | |
| 5,959,365 A | 9/1999 | Mantini et al. | |
| 6,386,038 B1 | 5/2002 | Lewis, III et al. | |
| 6,442,457 B1 | 8/2002 | Jones et al. | |
| 6,476,722 B1 | 11/2002 | Bidone | |
| 6,595,684 B1 | 7/2003 | Casagrande et al. | |
| 6,695,472 B1 | 2/2004 | Nayer | |
| 6,748,797 B2 | 6/2004 | Breed et al. | |
| 6,768,551 B2 * | 7/2004 | Mian et al. | 356/446 |
| 6,813,581 B1 | 11/2004 | Snyder | |
| 6,862,936 B2 * | 3/2005 | Kenderian et al. | 73/636 |
| 6,872,945 B2 | 3/2005 | Bartonek | |
| 6,883,962 B2 | 4/2005 | Kurata | |
| 6,909,514 B2 * | 6/2005 | Nayebi | 356/601 |
| 6,911,914 B2 | 6/2005 | Matthews, Jr. et al. | |
| 6,982,653 B2 | 1/2006 | Voeller et al. | |
| 6,985,803 B2 | 1/2006 | Abdel-Malek et al. | |
| 7,103,460 B1 | 9/2006 | Breed | |
| 7,132,653 B2 | 11/2006 | Faubion | |
| 7,254,482 B2 | 8/2007 | Kawasaki et al. | |
| 7,280,898 B2 | 10/2007 | Lesesky et al. | |
| 7,312,653 B2 | 12/2007 | Chen et al. | |
| 7,349,007 B2 | 3/2008 | Millar | |
| 7,507,965 B2 | 3/2009 | Lane et al. | |
| 7,564,569 B2 * | 7/2009 | Mian et al. | 356/601 |
| 7,602,506 B2 | 10/2009 | Hoffmann et al. | |
| 7,715,026 B2 | 5/2010 | Nayebi | |
| 8,006,559 B2 * | 8/2011 | Mian et al. | 73/643 |
| 2002/0097321 A1 | 7/2002 | McBride | |
| 2003/0214395 A1 | 11/2003 | Flowerday et al. | |
| 2005/0021283 A1 | 1/2005 | Brinton et al. | |
| 2005/0132587 A1 | 6/2005 | Larson et al. | |
| 2005/0145794 A1 | 7/2005 | Faubion | |
| 2005/0258943 A1 | 11/2005 | Mian et al. | |
| 2005/0259273 A1 | 11/2005 | Mian et al. | |
| 2005/0267707 A1 | 12/2005 | Mian et al. | |
| 2005/0270537 A1 | 12/2005 | Mian et al. | |
| 2006/0030985 A1 | 2/2006 | Lawida et al. | |
| 2006/0033985 A1 | 2/2006 | Mian | |
| 2006/0043296 A1 | 3/2006 | Mian et al. | |
| 2006/0091310 A1 | 5/2006 | Furry | |
| 2006/0114531 A1 | 6/2006 | Webb et al. | |
| 2006/0131464 A1 * | 6/2006 | Hesser et al. | 246/169 D |
| 2006/0170768 A1 | 8/2006 | Riley | |
| 2006/0180760 A1 | 8/2006 | Lane et al. | |
| 2007/0030349 A1 | 2/2007 | Riley | |
| 2007/0040911 A1 | 2/2007 | Riley | |
| 2007/0064244 A1 | 3/2007 | Mian et al. | |
| 2007/0075192 A1 | 4/2007 | Mian et al. | |
| 2007/0211145 A1 | 9/2007 | Kilian et al. | |
| 2008/0028846 A1 | 2/2008 | Heath et al. | |
| 2008/0143338 A1 | 6/2008 | Sekine et al. | |
| 2009/0018721 A1 * | 1/2009 | Mian et al. | 701/33 |
| 2009/0055041 A1 * | 2/2009 | Mian et al. | 701/29 |
| 2009/0055043 A1 * | 2/2009 | Mian et al. | 701/29 |
| 2009/0208059 A1 | 8/2009 | Geva et al. | |
| 2009/0290757 A1 * | 11/2009 | Mian et al. | 382/104 |
| 2010/0076631 A1 * | 3/2010 | Mian | 701/19 |
| 2011/0024576 A1 * | 2/2011 | Kilian et al. | 246/169 A |

OTHER PUBLICATIONS

Christiaen et al., "Evaluation of Infrared Brake Screening Technology: Final Report", U.S. Department of Transportation, Federal Motor Carrier Safety Administration, Dec. 2000, 90 pages.

Office Action, U.S. Appl. No. 11/748,714, Notification Date Feb. 18, 2010, 19 pages.

Athina Nickitas-Etienne, PCT International Preliminary Report on Patentability, Dated Apr. 26, 2011, 8 pages.

LaBatt, U.S. Appl. No. 11/748,714, Amendment, IEMC-0014, Jul. 3, 2012, 12 pages.

Jonathan M. Dager, USPTO Office Action, U.S. Appl. No. 11/748,714, Notification Date Mar. 1, 2012, 10 pages.

Dager, U.S. Appl. No. 11/748,714, Office Action Communication, Jul. 30, 2012, 19 pages.

Labatt, U.S. Appl. No. 11/748,714, Amendment to Office Action, Oct. 25, 2012, 14 pages.

* cited by examiner

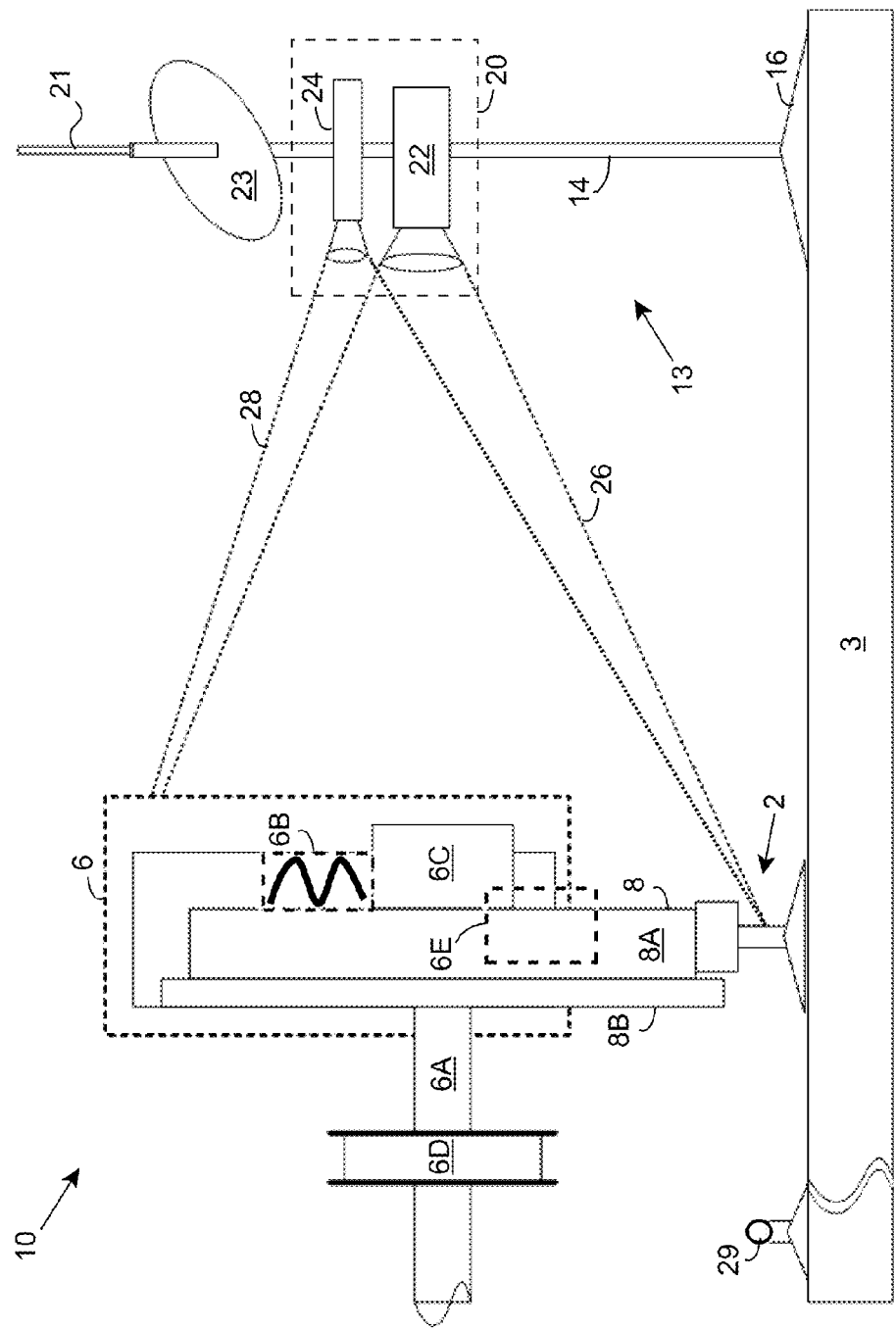

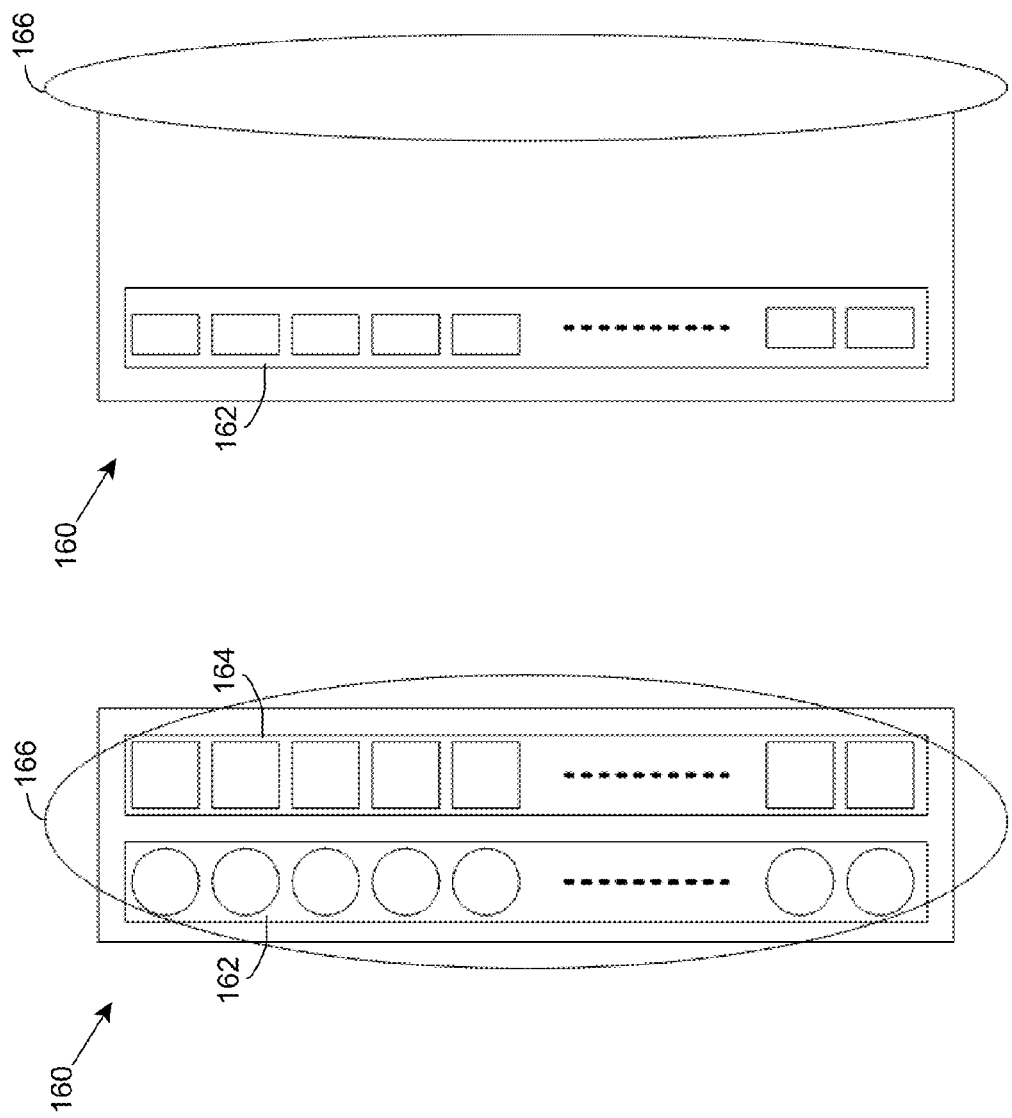

THERMAL IMAGING-BASED VEHICLE ANALYSIS

REFERENCE TO PRIOR APPLICATIONS

The current application claims the benefit of U.S. Provisional Application No. 61/193,012, titled "Infrared-based inspection of railway components", which was filed on 22 Oct. 2008, and which is hereby incorporated by reference. Aspects of the current application are also related to U.S. Utility application Ser. No. 11/748,714, titled "Vehicle evaluation using infrared data", which was filed on 15 May 2007, and which is hereby incorporated by reference.

TECHNICAL FIELD

The disclosure relates generally to thermal-imaging based analysis, and more particularly, to the analysis of various components of a vehicle using thermal image data.

BACKGROUND ART

Effective detection of one or more flaws in vehicles, such as rolling stock components in the rail industry, is highly desirable. For example, detection of flaws or problems with the wheels, brake components (including drums, discs, etc.), electronic brake control system, air conditioning units, transmission, driving motors, and/or the like, on rail vehicles is desirable so that corrective action(s) can be taken, e.g., to prevent a derailment, further damage, fire, or the like.

Current detectors include detectors that attempt to detect bearing overheating (e.g., hotbox detectors) and detectors that attempt to detect brake/wheel component overheating (e.g., hot wheel detectors). The rail industry has utilized hotbox detectors for an extended period of time to detect overheating bearings and thereby prevent derailment. These detectors are mounted on the rail or in close proximity to the rail to provide hot bearing and hot wheel data.

However, existing hotbox detectors have a high rate of false positives. Current detectors utilize single-element pyroelectric sensors, quad pyroelectric sensors, or a multi-element linear array of infrared (IR) sensors, each of which is generally an "on" or "off" sensor, to inspect wheels. These sensors do not produce very high signal amplitudes, which makes them relatively insensitive to variations. As a result, very high threshold temperatures are used to limit the number of false positives. The sensors also tend to respond slowly, giving no response of significance if a rail vehicle stops. Furthermore, such sensors do not acquire detailed information on the wheel and surrounding areas (e.g., brake and suspension elements, undercarriage, etc.). As a result of the limited data available from current sensors, sources of noise, outside influences, and other sources of errors, cannot be identified.

The current sensors frequently require that the rail vehicles be moving at a relatively constant speed in order to provide meaningful data. As a result, hotbox detectors are typically installed on a mainline. In response to a hotbox detector indicating the presence of overheating bearings, a train is required to stop so that the hotbox can be inspected. However, any faulty part often cannot be readily repaired. Additionally, a false positive in this scenario can cost thousands of dollars per occurrence due to delays, inspections, disruptions, and the like. For example, an alarm can be triggered by an overheating air conditioning unit on a rail vehicle. In this case, the detector can indicate that a problem exists on a particular rail vehicle. However, the source of the problem can only be determined after an often difficult and time consuming (and therefore costly) hands-on inspection of the rail vehicle. When the source of the alarm does not threaten derailment, as in the case of an overheating air conditioning unit, such an alarm results in significant cost, without a corresponding improvement in safety.

Some approaches seek to utilize signal processing schemes to reduce the number of errors and false positives. For example, one dimensional (1D) signal processing has been proposed to address some errors. However, these approaches fail to provide protection against many false alarms.

SUMMARY OF THE INVENTION

In general, the inventors recognize that current approaches for evaluating vehicles, such as rail vehicles, are error prone. As a result, very high threshold temperatures are used as a work around to prevent excessive false positives, resulting in some errors not being detected. However, even these high threshold temperatures do not prevent some false positives, resulting in costly disruptions to rail travel.

Unlike prior approaches, the inventors propose to use thermal imaging, e.g., mid-wave infrared (MWIR) or long-wave infrared (LWIR) image data, to acquire diagnostic information on passing vehicles, such as rail vehicles. The diagnostic information can be processed to determine the relative operating "health" of various components of the rail vehicle, including for example, a wheel, a brake, a suspension, a coupling, a bearing, and/or the like. For example, various intelligent/smart sensor methodologies can be applied to the thermal image data to automatically or semi-automatically detect, diagnose, and/or alert other systems/users of the presence of one or more potential or actual problems with a rail vehicle.

In an illustrative implementation of an embodiment of the invention, infrared image data is acquired for rail vehicles in a classification yard. The images acquired are then subjected to sophisticated image analysis and this analysis used to accurately determine the presence or absence of the various flaws or faults described previously. Unlike prior approaches, embodiments of the invention: enable analysis of components of rail vehicles at very slow to moderate speeds (e.g., in a classification yard), enable the detection and classification of smaller temperature differences as faults, use pattern recognition processes to substantially reduce false positives/negatives, enable the detection of additional types of faults and differentiation between faults, do not require installation of sensing components on or in close proximity to the rail (and therefore is not adversely impacted by vibrations), enable the fusion of lower resolution infrared image data with higher resolution visible image data to increase comprehension and analysis of the data, and/or the like.

Aspects of the invention provide a solution for analyzing a vehicle using multi-dimensional infrared image data acquired for the vehicle. A component of the vehicle can be identified within the infrared image data, and the infrared image data for the component can be analyzed to determine whether any condition(s) are present on the vehicle. One or more actions can be initiated in response to a determination that a particular condition is present. Additionally, visible image data can be used to supplement the infrared image data. Still further, infrared image data for similar components imaged concurrently with the component can be used to identify whether any condition(s) are present on the vehicle. Unlike prior art approaches in the rail industry, the analysis can be performed on rail vehicles within a classification yard.

A first aspect of the invention provides a system for analyzing a vehicle, the system comprising: a component configured to process multi-dimensional infrared image data for the vehicle, wherein the component configured to process includes: a component configured to identify at least one component of the vehicle in the infrared image data; and a component configured to determine whether any one of a set of conditions are present on the vehicle based on the infrared image data of the at least one component; and a component configured to determine a set of actions in response to a determination that at least one of the set of conditions is present on the vehicle.

A second aspect of the invention provides a classification yard including: at least one infrared imaging device for acquiring multi-dimensional infrared image data for a rail vehicle in the classification yard; a component configured to process the infrared image data for the rail vehicle, wherein the component configured to process includes: a component configured to identify at least one component of the rail vehicle in the infrared image data; and a component configured to determine whether any one of a set of conditions are present on the rail vehicle based on the infrared image data of the at least one component; a component configured to determine a set of actions in response to a determination that at least one of the set of conditions is present on the rail vehicle; and a component configured to provide the set of actions for processing by a control center of the classification yard in response to the determination.

A third aspect of the invention provides a system for analyzing a vehicle, the system comprising: a component configured to process multi-dimensional infrared image data for the vehicle, wherein the component configured to process includes: a component configured to identify a first component of the vehicle in the infrared image data; and a component configured to determine whether any one of a set of conditions are present on the vehicle based on the infrared image data of the first component, wherein the component configured to determine compares the infrared image data of the first component to infrared image data for a plurality of other components of the same type as the first component to determine whether at least one of the set of conditions is present; and a component configured to determine a set of actions in response to a determination that at least one of the set of conditions is present on the vehicle.

A fourth aspect of the invention provides a method for analyzing a vehicle, the method comprising: processing multi-dimensional infrared image data for the vehicle, wherein the processing includes: identifying at least one component of the vehicle in the infrared image data; and determining whether any one of a set of conditions are present on the vehicle based on the infrared image data of the at least one component; and determining a set of actions in response to a determination that at least one of the set of conditions is present on the vehicle.

Other aspects of the invention provide methods, systems, program products, and methods of using and generating each, which include and/or implement some or all of the actions described herein. The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIGS. 1A and 1B show perspective and side views, respectively, of a portion of an illustrative thermal imaging-based rail vehicle analysis system according to an embodiment.

FIG. 13 shows front and side views of an illustrative multi-spectral imaging device according to an embodiment.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution for analyzing a vehicle using multi-dimensional infrared image data acquired for the vehicle. A component of the vehicle can be identified within the infrared image data, and the infrared image data for the component can be analyzed to determine whether any condition(s) are present on the vehicle. One or more actions can be initiated in response to a determination that a particular condition is present. Additionally, visible image data can be used to supplement the infrared image data. Still further, infrared image data for similar components imaged concurrently with the component can be used to identify whether any condition(s) are present on the vehicle. Unlike prior art approaches in the rail industry, the analysis can be performed on rail vehicles within a classification yard. As used herein, unless otherwise noted, the term "set" means one or more (i.e., at least one) and the phrase "any solution" means any now known or later developed solution.

Figure 1A:
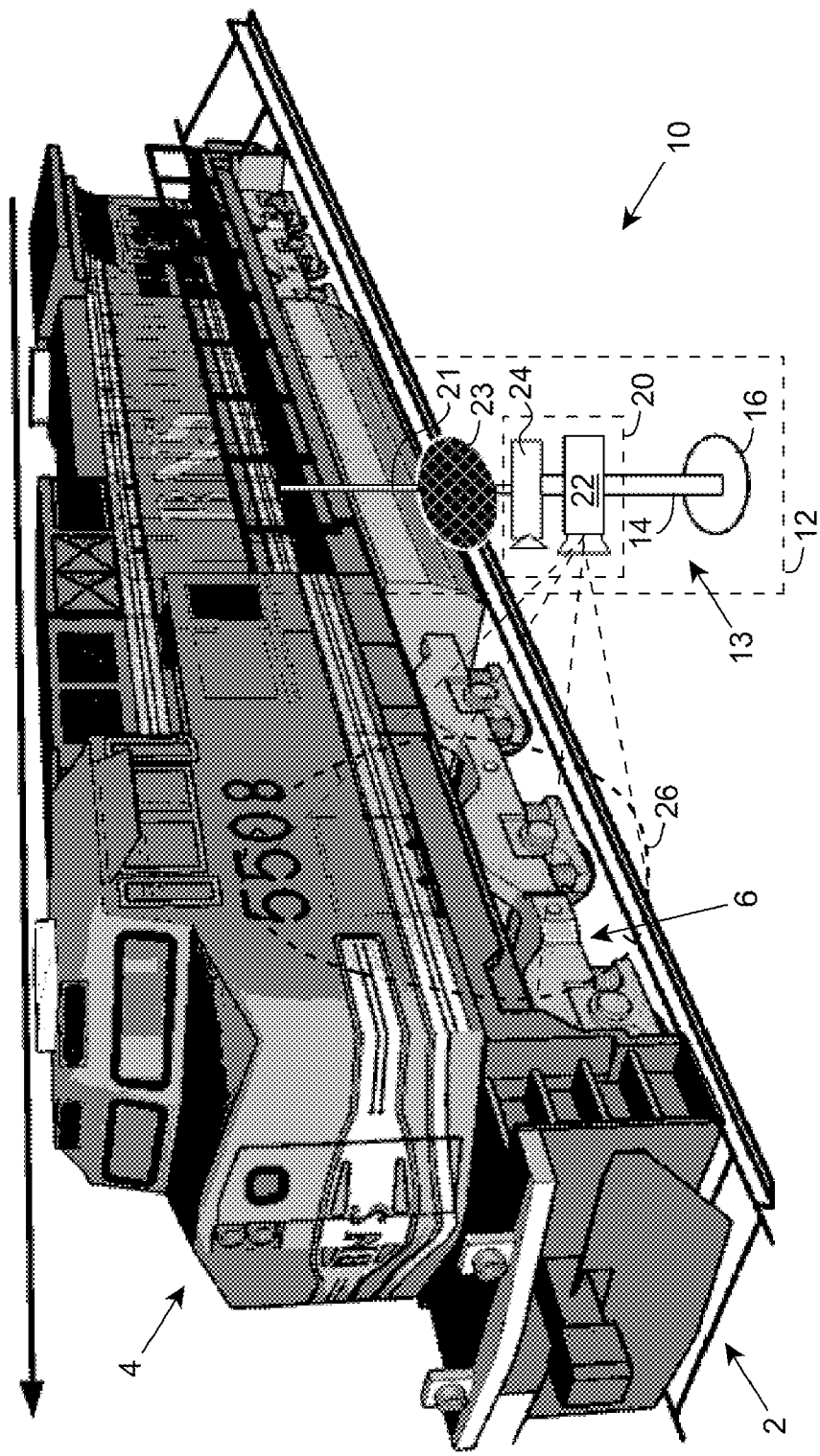

Turning to the drawings, FIGS. 1A and 1B show perspective and side views, respectively, of a portion of an illustrative thermal imaging-based rail vehicle analysis system 10 according to an embodiment. As illustrated system 10 includes an acquisition subsystem 12. Acquisition subsystem 12 includes an instrumentation emplacement 13, which comprises a support structure 14 and a base structure 16. The emplacement 13 can be permanently installed adjacent to a set of tracks 2, e.g., within the ballast 3 supporting the set of tracks 2, or temporarily placed adjacent to the set of tracks 2, on which rail vehicles 4 travel. Further, acquisition subsystem 12 can include multiple instrumentation emplacements 13 (e.g., one on each side of the set of tracks 2), although a single instrumentation emplacement 13 may be sufficient (e.g., to acquire infrared image data for an axle, which may be the primary component of interest). In an embodiment, support structure 14 can facilitate easy adjustment of the height and/or angles of one or more of the set of analysis devices 20 supported by the support structure 14, e.g., to facilitate easy set up (e.g., for a portable instrumentation emplacement 13), calibration, and/or the like.

By mounting the set of analysis devices 20 on support structure 14, fouling of the various devices by environmental conditions, such as mud, snow, rain, and/or the like, can be significantly reduced over alternative approaches. Additionally, emplacement 13 can include additional protection for the set of analysis devices 20, such as boxes, hoods, wipers, and/or the like, which can further reduce any fouling. In an embodiment, support structure 14 comprises a pole, such as a galvanized steel pole, on which a set of analysis devices 20 can be mounted using any solution. The pole can be sufficiently high, e.g., approximately four feet, to enable a desired angle of imaging of the relevant portions of the rail vehicle 4. The base structure 16 can comprise a concrete foundation, or the like, frequently used for mounting railway equipment. Furthermore, the base structure 16 can include shock and vibration isolation mechanism(s), such as rubber dampers, to reduce vibration in the set of analysis devices 20 induced by the rail traffic. Regardless, it is understood that support structure 14 and base structure 16 can be any structure sufficiently sturdy to hold the various set of analysis devices 20 steady during various operating conditions that may be experienced. Each device in the set of analysis devices 20 can be mounted to the support structure 16 using clamps, u-bolts, brackets, and/or the like.

The set of analysis devices 20 is shown including an infrared imaging device 22 and a second imaging device 24. Imaging devices 22, 24 are positioned to capture image data for the wheel trucks 6 of a rail vehicle 4 that is moving along tracks 2. For example, support structure 14 can be located at a distance from tracks 2 that enables imaging devices 22, 24 to capture image data having fields of view 26, 28, respectively, in which the wheel trucks 6 are fully visible. As illustrated, support structure 14 and imaging devices 22, 24 can be located such that at a distance at which support structure 14 is placed from rail vehicles 4, imaging devices 22, 24 have fields of view 26, 28, respectively, that are closely co-registered in a plane of the passing rail vehicles 4, and particularly a plane of the wheels 8.

Various portions of wheel trucks 6 and wheels 8 may be analyzed by analysis system 10 using thermal image data of the wheel trucks 6 and wheels 8. For example, each wheel 8 includes a tread 8A and a flange 8B. Further, the wheel truck 6 includes an axle 6A and suspension components, such as springs 6B. Axle 6A includes a hub bearing 6C attached thereto, on which rail wheels 8 turn. The axle 6A also can have discs 6D for a rotary disc braking system attached, which are commonly used in transit rail vehicles. Further, wheel truck 6 may include pads 6E of a tread brake system that press against tread 8A to slow the rail vehicle 4.

As illustrated, imaging devices 22, 24 can be mounted to support structure 14 such that the fields of view are substantially perpendicular to the set of tracks 2. However, it is understood that imaging devices 22, 24 can be mounted to support structure 14 such that the train 4 and components thereof are imaged from an angle. In the latter case, one or more components of the wheel truck 6, such as a disc 6D for rotary disc brakes, can be imaged in the image data. Additionally, one or more imaging devices 22, 24 can comprise a wide-angle/ultra wide-angle imaging device that can acquire image data having a field of view substantially perpendicular to the set of tracks 2, but which includes image data of various components from an angle in the end portions of the field of view. In this case, imaging devices 22, 24 can capture oblique/off-axis image data having more detail on components such as the brakes, suspension, undercarriage, opposite wheel, etc. Further, the oblique/off-axis image data can enable easier identification of hot spots on the tread 8A.

To facilitate calibration of the infrared imaging device 22, an embodiment includes a known temperature source 29, which can be installed in the interior of the set of tracks 2. Infrared imaging device 22 can be installed in a manner that the known temperature source 29 is directly visible at various times during operation, e.g., when no rail vehicle 4 is passing or between the wheel trucks 6 of a rail vehicle. The known temperature source 29 can have a substantially constant known temperature, a known variable temperature, or the like. The temperature source 29 can comprise, for example, a black body simulator, such as those available from Omega and other black body suppliers. The temperature source 29 can be set to a temperature within the approximate temperature range of interest to be imaged by the infrared imaging device 22, for example, approximately 150 degrees F. Alternatively, the temperature source 29 can be set at multiple temperatures corresponding to a range of infrared imaging device 22 operation, for example, the ambient temperature to approximately 500 degrees F. The particular temperature(s) of temperature source 29 can be adjusted based on the ambient temperature of the operating environment. For example, in extremely cold temperatures (e.g., −20 degrees F.), the temperature range of interest will be substantially lower than in extremely warm temperatures (e.g., 110 degrees F.). As a result, the temperature(s) of temperature source 29 can be adjusted accordingly.

In an embodiment, infrared imaging device 22 comprises a thermal imaging, e.g., mid-wave infrared (MWIR) or long-wave infrared (LWIR) device, which is configured to capture infrared image data of wheel trucks 6 and rail wheels 8 of passing rail vehicles 4. For example, infrared imaging device 22 can comprise a microbolometer. Infrared imaging device 22 can comprise any resolution, which can be selected based on the desired analysis of the image data, other sensing devices (if any) being utilized, and/or the like. To this extent, infrared imaging device 22 can capture image data having a resolution as low as 4×4 pixels, a relatively high resolution of 640×480 pixels, or higher.

In an embodiment, the second imaging device 24 comprises a visible light imaging device having a higher resolution than infrared imaging device 22. For example, the second imaging device 24 can comprise a resolution of 640×480 pixels (also known as VGA resolution) or higher, and capture images at approximately thirty frames per second (fps) or higher, e.g., up to many thousands of frames per second. Imaging devices 22, 24 can be configured to capture image data substantially simultaneously. In this case, an effective resolution of infrared imaging device 22 and an understanding of a source of heat can be increased using a visible image overlay, such as that described in U.S. Pat. No. 7,208,733, which is incorporated by reference.

Infrared imaging device 22 also can comprise a high-speed imaging device capable of operating at a rate higher than 30 fps, e.g., approximately 100 fps or more. In an embodiment, infrared imaging device 22 comprises a high-speed imaging microbolometer capable of obtaining sharp images of the target wheels 8 traveling at speeds from zero up to 250 miles per hour. For example, such devices are currently available from infrared imaging companies such as ULIS and DIAS. Use of a highly sensitive microbolometer instead of, for example, a few-element pyroelectric sensor, enables the acquisition of image data capable of distinguishing very small temperature differentials as small as 0.1 degrees F. Additionally, the use of an array of such microbolometers enables the acquisition of low-noise, high-detail thermal images of the rail vehicle 4 and its components.

As illustrated, instrumentation emplacement 13 can include various components in addition to imaging devices 22, 24. To this extent, the set of analysis components 20 can include one or more devices for capturing non-image data of a passing rail vehicle 4. For example, illustrative devices include a radio frequency identification (RFID) tag reader configured to read a RFID tag associated with a rail vehicle 4, a microphone configured to capture sounds made by a passing rail vehicle 4, and/or the like.

Additionally, instrumentation emplacement can include various devices that support operation of the set of analysis components 20. For example, instrumentation emplacement 13 can comprise a transceiver and a corresponding antenna 21 for communicating with a data processing system, e.g., to transmit data acquired by the set of analysis components 20 for processing by the data processing system. Additionally, instrumentation emplacement 13 can comprise a power source for the set of various devices. In an embodiment, the power source comprises a solar panel 23, although any power source or combination of power sources, including batteries or connection to an electrical grid, can be utilized.

Figure 2:
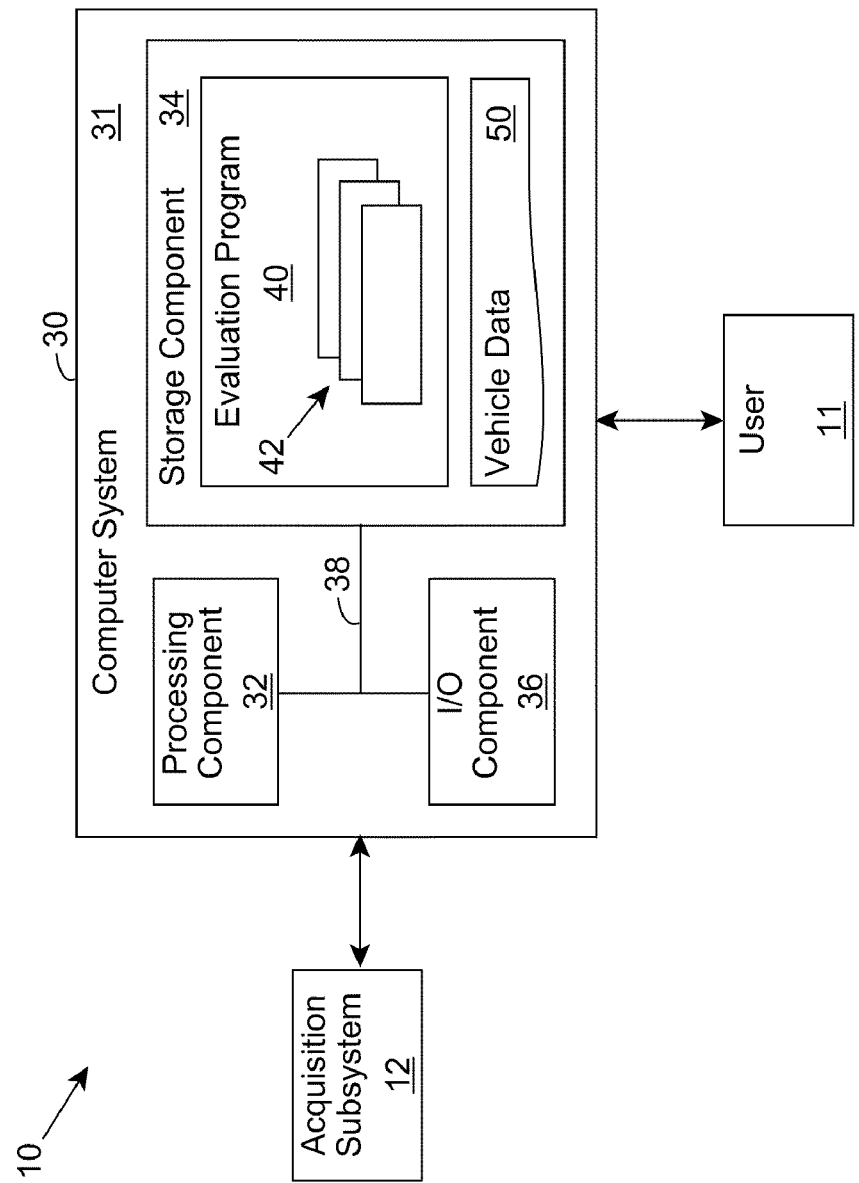
FIG. 2 shows a schematic view of an illustrative thermal imaging-based rail vehicle analysis system according to an embodiment.

FIG. 2 shows a schematic view of an illustrative thermal imaging-based rail vehicle analysis system 10 according to an embodiment. To this extent, system 10 includes an analysis subsystem 30, which is implemented as a computer system 31, in communication with acquisition subsystem 12. Analysis subsystem 30 can receive vehicle data 50, including thermal imaging data, from acquisition subsystem 12 and perform a process described herein in order to analyze one or more attributes of an imaged vehicle, such as rail vehicle 4. In particular, computer system 31 is shown including an evaluation program 40, which makes computer system 31 operable to analyze one or more attributes of the imaged rail vehicle 4 by performing a process described herein.

Computer system 31 is shown including a processing component 32 (e.g., one or more processors), a storage component 34 (e.g., a storage hierarchy), an input/output (I/O) component 36 (e.g., one or more I/O interfaces and/or devices), and a communications pathway 38. In general, processing component 32 executes program code, such as evaluation program 40, which is at least partially fixed in storage component 34. While executing program code, processing component 32 can process vehicle data 50, which can result in reading and/or writing transformed vehicle data 50 from/to storage component 34 and/or I/O component 36 for further processing. Pathway 38 provides a communications link between each of the components in computer system 31. I/O component 36 can comprise one or more human I/O devices, which enable a human user 11 to interact with computer system 31 and/or one or more communications devices to enable a system user 11 to communicate with computer system 31 using any type of communications link. To this extent, evaluation program 40 can manage a set of interfaces (e.g., graphical user interface(s), application program interface, and/or the like) that enable human and/or system users 11 to interact with evaluation program 40. Further, evaluation program 40 can manage (e.g., store, retrieve, create, manipulate, organize, present, etc.) the data, such as vehicle data 50, using any solution.

In any event, computer system 31 can comprise one or more general purpose computing articles of manufacture (e.g., computing devices) capable of executing program code, such as evaluation program 40, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, evaluation program 40 can be embodied as any combination of system software and/or application software.

Further, evaluation program 40 can be implemented using a set of modules 42. In this case, a module 42 can enable computer system 31 to perform a set of tasks used by evaluation program 40, and can be separately developed and/or implemented apart from other portions of evaluation program 40. As used herein, the term "component" means any configuration of hardware, with or without software, which implements the functionality described in conjunction therewith using any solution, while the term "module" means program code that enables a computer system 31 to implement the functionality described in conjunction therewith using any solution. When fixed in a storage component 34 of a computer system 31 that includes a processing component 32, a module is a substantial portion of a component that implements the functionality. Regardless, it is understood that two or more components, modules, and/or systems may share some/all of their respective hardware and/or software. Further, it is understood that some of the functionality discussed herein may not be implemented or additional functionality may be included as part of computer system 31.

When computer system 31 comprises multiple computing devices, each computing device can have only a portion of evaluation program 40 fixed thereon (e.g., one or more modules 42). However, it is understood that computer system 31 and evaluation program 40 are only representative of various possible equivalent computer systems that can perform a process described herein. To this extent, in other embodiments, the functionality provided by computer system 31 and evaluation program 40 can be at least partially implemented by one or more computing devices that include any combination of general and/or specific purpose hardware with or without program code. In each embodiment, the hardware and program code, if included, can be created using standard engineering and programming techniques, respectively.

Regardless, when computer system 31 includes multiple computing devices, the computing devices can communicate over any type of communications link. Further, while performing a process described herein, computer system 31 can communicate with one or more other computer systems, such as acquisition subsystem 12 and user 11, using any type of communications link. In either case, the communications link can comprise any combination of various types of wired and/or wireless links; comprise any combination of one or more types of networks; and/or utilize any combination of various types of transmission techniques and protocols.

As discussed herein, evaluation program 40 enables computer system 31 to process thermal imaging data acquired by acquisition subsystem 12 to analyze one or more attributes of an imaged vehicle, such as rail vehicle 4. To this extent, various aspects of an illustrative evaluation program 40 and computer system 31 are shown and described in U.S. Utility application Ser. No. 11/748,714, which is hereby incorporated by reference. It is understood that any and all techniques and approaches described in U.S. Utility application Ser. No. 11/748,714 can be implemented by system 10.

Figure 3:
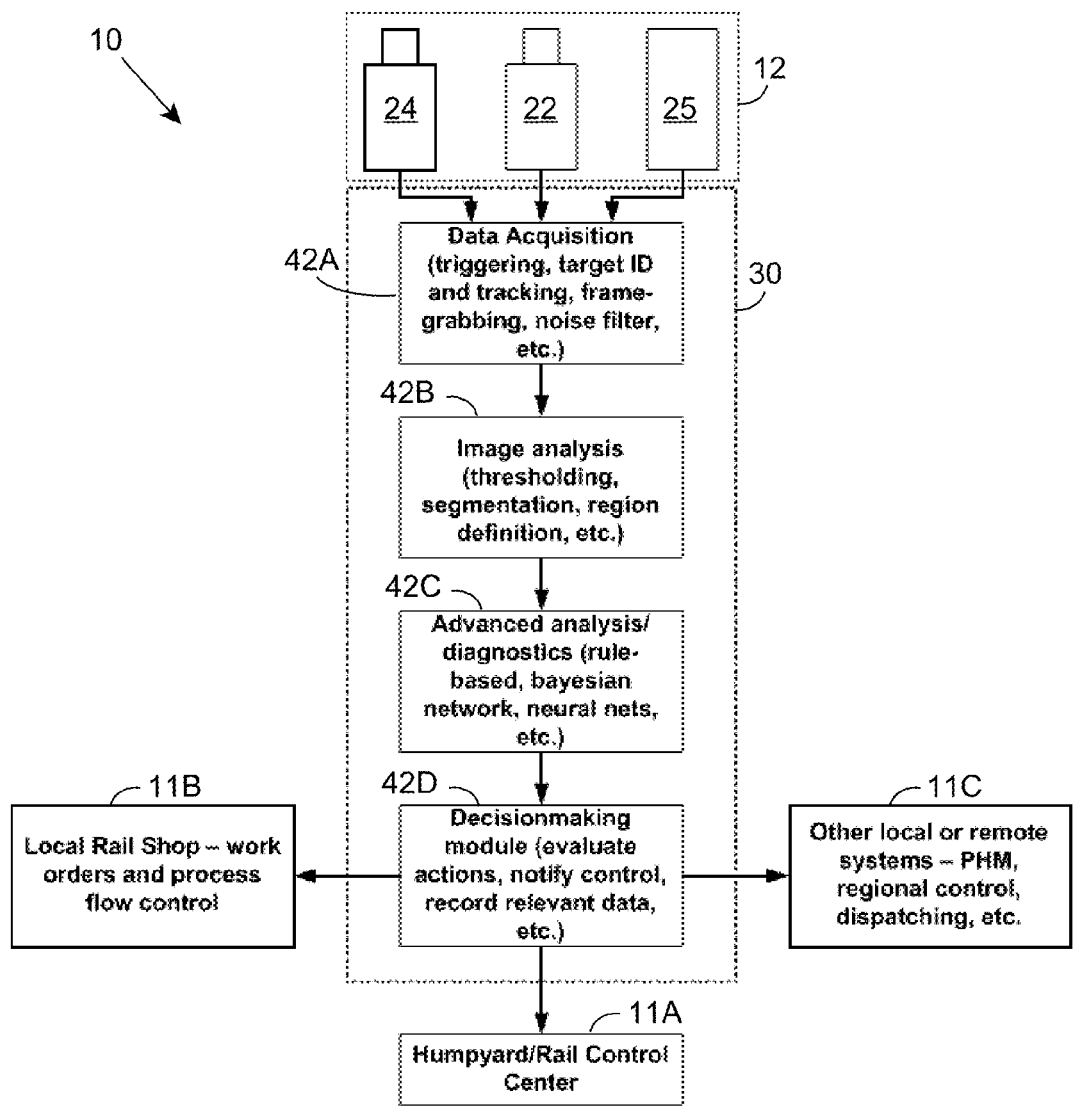
FIG. 3 shows an illustrative data flow diagram for performing thermal imaging-based rail vehicle analysis according to an embodiment.

Regardless, FIG. 3 shows an illustrative data flow diagram for performing thermal imaging-based rail vehicle analysis according to an embodiment. As illustrated, analysis subsystem 30 includes various components 42A-42D. Each component 42A-42D can be implemented using one or more modules 42 (FIG. 2) of evaluation program 40 (FIG. 2) and general purpose processing hardware, as special purpose hardware, and/or the like. As illustrated, vehicle data 50 on a passing rail vehicle 4 is acquired by acquisition subsystem 12, and provided to analysis subsystem 30 for processing. Analysis subsystem 30 can further provide vehicle data 50 based on the processing for use by one or more user systems 11A-11C.

A data acquisition component 42A of analysis subsystem 30 can acquire the vehicle data 50 on a passing rail vehicle 4 from the various devices of acquisition subsystem 12. To this extent, data acquisition component 42A is shown receiving data from an infrared imaging device 22, a second imaging device 24 (e.g., a visible imaging device), and one or more non-image data capture devices 25, such as an RFID device, an acoustic sensing system, wheel sensors, and/or the like. Data acquisition component 42A can perform pre-processing on the acquired vehicle data 50. For example, data acquisition component 42A can filter noise from the raw vehicle data 50, determine an identity of the passing rail vehicle and associate the identity to the acquired vehicle data 50, and/or the like. Additionally, it is understood that data acquisition component 42A can control the operation of acquisition subsystem 12. For example, data acquisition component 42A can receive a signal from a vehicle sensing system of an approaching set of rail vehicles 4, and trigger the devices of acquisition subsystem 12 to initialize. Similarly, data acquisition component 42A can determine when no additional rail vehicles 4 are approaching and trigger the devices of acquisition subsystem 12 to shut down/sleep.

Data acquisition component 42A can provide the pre-processed vehicle data 50 on the rail vehicle 4 for processing by an analysis component 42B. Analysis component 42B can perform any combination of one or more image analysis operations on the image vehicle data 50 including, but not limited to, thresholding, edge detection, region definition and segmentation, and/or the like. Additionally, analysis component 42B can perform various analysis operations on non-image vehicle data 50 acquired for the rail vehicle 4 including, but not limited to, wavelet analysis for acoustic data to locate the precise timing of a detected event within a data stream, determination of an envelope around the amplitude or frequency domain components of the acoustic data to identify a signal, and/or the like.

Analysis component 42B, can provide the processed vehicle data 50 and/or raw vehicle data 50 for processing by advanced analysis component 42C. Advanced analysis component 42C can evaluate the results of the analysis performed by analysis component 42B using any solution. For example, advanced analysis component 42C can perform rule-based analysis (e.g., if region A temp>region B temp+X degrees, then . . . ), Bayesian or neural network processing, and/or the like, to determine whether one or more conditions (e.g., flaws) exist on a particular rail vehicle 4.

Advanced analysis component 42C can provide the results of the determination of the existence or non-existence of the set of conditions on rail vehicle 4 for processing by decision making component 42D. Decision making component 42D can determine what action(s) are to be performed in response to the set of conditions present on the rail vehicle. Decision making component 42D can implement any solution for determining the action(s) based on the set of conditions including, for example, a complex automated expert system, a rule-based system, and/or the like. Analysis component 42C can utilize one of various solutions, which can vary considerably depending on the operating environment, for determining/diagnosing faults. To this extent, analysis component 42C can use different rule sets (fuzzy or fixed) for different settings or operating conditions (e.g., winter versus summer, cold versus warm, etc.). Additionally, analysis component 42C can utilize different rule sets depending on the typical characteristics of the passing rail vehicles (e.g., on main line or hump yard, downhill or flat, etc.).

Similarly, the appropriate action(s) for a given condition can vary based on an implementation of system 10. Illustrative actions include, but are not limited to, allowing the rail vehicle 4 to pass (e.g., when no dangerous conditions are identified), flagging the rail vehicle 4 for later inspection (e.g., when potential dangerous condition is identified), indicating the rail vehicle 4 should be removed from a consist (e.g., for in situ or local repair), indicating the rail vehicle 4 should be routed to a repair track, indicating that a train should slow down/stop to avoid derailment, and/or the like.

Regardless, decision making component 42D can provide the appropriate action(s), if necessary, for processing by one or more user systems 11A-11C. For example, when implemented within a rail yard, decision making component 42D can communicate the action(s) to a control center 11A of the rail yard (e.g., hump yard) for proper routing of the rail vehicle, a local repair shop 11B of the rail yard for preparing to repair one or more identified defects, and/or the like. In response, individuals within the rail yard can take the necessary action(s) to route and/or perform repair(s) on the rail vehicle 4. Additionally, decision making component 42D can provide data on the rail vehicle for processing by another analysis/action system 11C, such as a predictive health maintenance (PHM) system for a captive fleet. The analysis/action system 11C can gather data about the long-term operation of a fleet of rail vehicles 4, and perform regional control operations for the fleet, such as dispatching/adjusting shipping schedules, allocating replacement rail vehicles, and/or the like.

As discussed herein, analysis component 42B performs image processing on the infrared (and visible) image vehicle data 50 acquired by acquisition subsystem 12 to identify and analyze features in the image vehicle data 50. Additionally, through the presence and characteristics of these features, advanced analysis component 42C can determine whether any particular conditions or faults of interest are indicated by the image data. Such image data processing has been described in detail in U.S. Pat. Nos. 7,355,508 and 7,208,733 and U.S. Utility application Ser. No. 11/748,714, each of which is incorporated by reference. In general, an embodiment of the image processing includes performing edge detection and segmentation upon an image (e.g., using thresholding processes), assembling/recognizing individual segments as part of one or more features (feature extraction), and assembling the features into "blobs" or objects, which can be compared against known likely objects using, for example, templating, expert system recognition, and/or the like.

Figure 4:
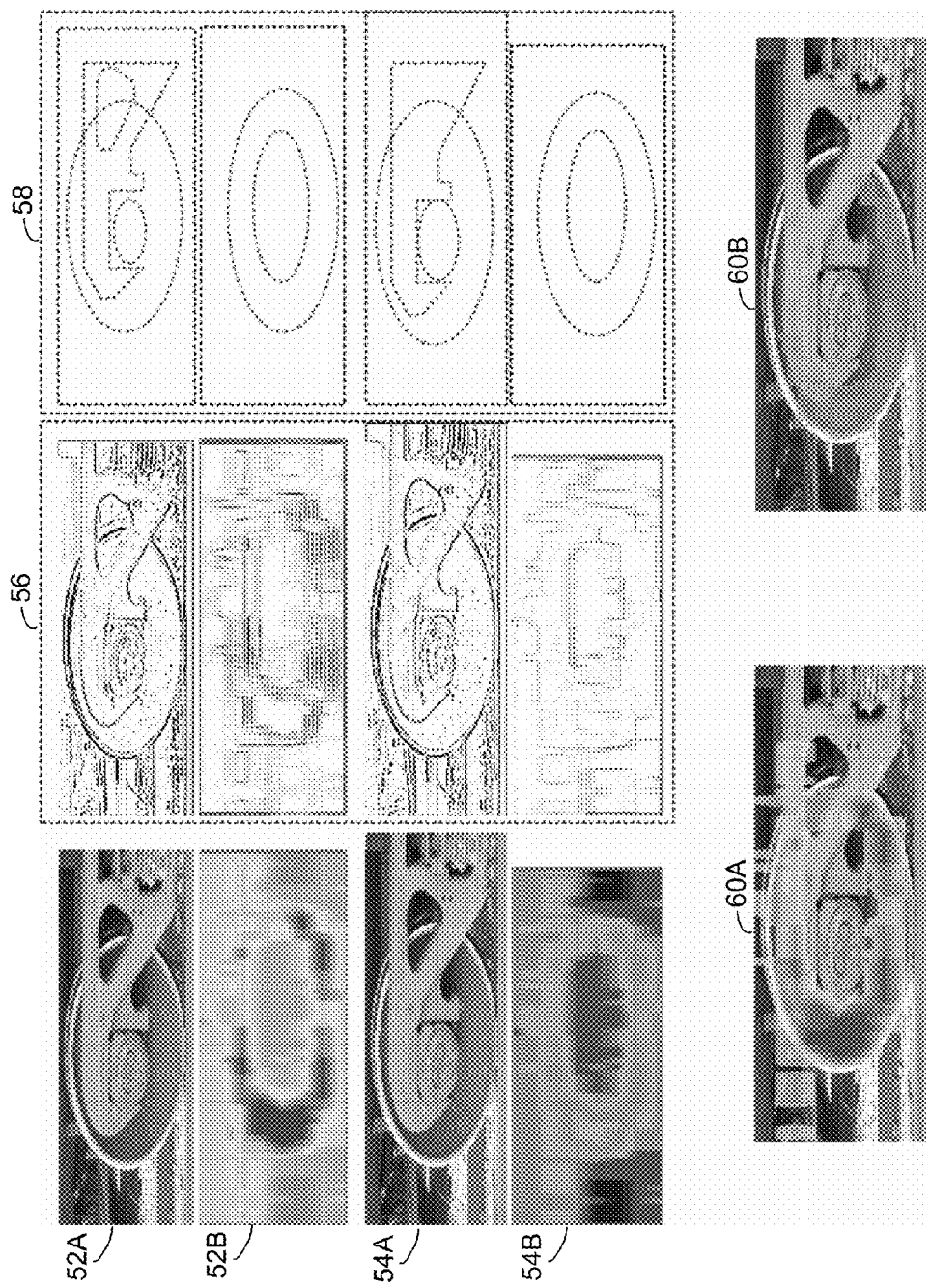
FIG. 4 shows an illustrative set of examples of infrared image processing according to an embodiment.

FIG. 4 shows an illustrative set of examples of infrared image processing, which illustrate the processing that can be performed by analysis component 42B and/or advanced analysis component 42C of FIG. 3, according to an embodiment. Images 52A, 54A are vertically-compressed visible light images of two passing rail wheels 8 (FIG. 1B). Images 52A, 54A can be acquired by a two-dimensional visible imaging device 24 (FIG. 1B). Alternatively, images 52A, 54A can be produced by a time-synchronized vertical linear array, which can assemble the two-dimensional images 52A, 54A from one-dimensional linear images sequentially acquired by a visible imaging device 24.

Regardless, images 52B, 54B are lower resolution infrared images of the same rail wheels 8 as images 52A, 54A, respectively, which have also been vertically compressed to the same degree as images 52A, 54A, respectively. Images 52B, 54B can be acquired by infrared imaging device 22 (FIG. 1B). Image 52B indicates that the corresponding wheel 8 is a hot wheel, while image 54B shows a much cooler wheel 8. However, it is very difficult to determine what was imaged in images 52B, 54B without an understanding of the exact nature of the image, which may not be readily available for any given relatively low-resolution infrared image 52B, 54B acquired while a train is moving.

In an embodiment, analysis component 42B performs image fusion, which permits a single image to retain the relevant information from two or more types of sensor data, e.g., infrared and visible image data. For example, analysis component 42B can implement a process that produces easily understandable images 60A, 60B showing which wheel 8 is overheating. To this extent, analysis component 42B can generate image group 56 by processing each of the corresponding images 52A, 52B, 54A, 54B to extract line edges, enhance contrast, remove extraneous data, and/or the like. Analysis component 42B can use a different solution for determining line edges when processing different types of images. For example, when processing visible light images 52A, 54A, analysis component 42B can determine line edges based on the levels and rate of change of actual scene brightness or contrast. In contrast, when processing infrared images 52B, 54B, analysis component 42B can determine line edges based on direct analysis of the temperatures and differences in temperatures.

Analysis component 42B can generate image group 58 by processing the images in image group 56, e.g., using a templating solution, to locate features that are expected in each image in image group 56. For example, the features can include an elliptical (compressed circle) feature for a wheel, and other features that are part of the wheel truck 6 (FIG. 1A). Analysis component 42B can use the location of these features to select the relevant portions of the infrared images 52B, 54B, e.g., areas in which the infrared images show significant temperature differentials, and superimpose those portions on the corresponding visible light images 52A, 54A. The end results are image 60A, which shows the hottest portions of image 54A superimposed on image 52A, and image 60B, which is a combination of the warmest portions of image 54B with image 54A.

Analysis component 42B and/or advanced analysis component 42C can perform various processes to analyze data acquired by acquisition subsystem 12. For example, advanced analysis component 42C can analyze an individual image of a rail wheel 8 for anomalies. In particular, a typical rail wheel 8 and wheel truck 6 will present a generally similar profile at the same point in travel along a set of tracks 2. After detection and definition of edges and features by analysis component 42B, advanced analysis component 42C can compare the identified features of the wheel 8 and related assemblies to a typical profile. Advanced analysis component 42C can flag a wheel 8 or wheel truck 6 showing aberrations beyond some minimum limit for further analysis. For image data in which a component, such as the tread surface of the wheel, is not directly imaged, analysis component 42B can analyze the pattern of heat for "bleed through", in which heat begins to radiate through an imaged object, such as the wheel rim, starting at the approximate location of the non-imaged component.

Advanced analysis component 42C also can process vehicle data 50 acquired by acquisition subsystem 12 to determine whether a wheel 8 is rotating properly. For example, advanced analysis component 42C can determine the diameter of a wheel from a visible image using attributes of the rail environment and imaging setup. Additionally, acquisition subsystem 12 can include sensors configured to acquire a speed of the rail vehicle and a rotational speed of the wheel 8, which acquisition subsystem 12 can provide for evaluation by analysis subsystem 30. Alternatively, analysis component 42B can track movement of a feature of a wheel 8 and the wheel itself through multiple images to determine a speed of the rail vehicle and/or a rotational speed, if any, of the wheel 8. Advanced analysis component 42C can determine an expected rotational speed based on the diameter and the speed of the rail vehicle. Advanced analysis component 42C can flag any significant deviation (e.g., greater than approximately +/−ten percent) between the expected and measured rotational speeds as a possible indication of some form of sticking on the part of the wheel 8.

Additionally, data acquisition component 42A can calibrate the infrared image data to measure actual temperatures. For example, analysis component 42B can calibrate the infrared image data with infrared image data for a known temperature source 29. Alternatively, analysis component 42B can implement a radiometric temperature solution using infrared image data acquired by: multiple collocated infrared imaging devices (e.g., infrared imaging device 22 and second imaging device 24) having substantially the same fields of view, but through different filters; a single infrared imaging device 22 with a tunable filter or filter wheel that enables imaging the rail vehicle in different bands; and/or the like. For example, the rail vehicle can be imaged in two or more bands comprising: the near infrared band below approximately two microns, the short wave infrared band between approximately two to five microns, a long wave band between approximately eight to twelve microns, and larger than twelve micron wavelengths. In any event, analysis component 42B can construct a temperature map based on the infrared image data, which advanced analysis component 42C can use to determine how badly overheated a particular rail vehicle component may be. Since some heating of rail vehicle components will occur during normal operation, it may be desirable to distinguish between, for example, normal heating of bearings 6C (especially on cold days, when the apparent differential may be large) and abnormal heating of bearings 6C due to wear.

Data acquisition component 42A can perform various processing on the infrared image data acquired by acquisition subsystem 12. For example, an imaged wheel tread 8A and/or rail may be extremely smooth and shiny, and therefore act as an infrared mirror. In this case, the resulting infrared image data may yield confusing readings. Acquisition subsystem 12 can include infrared/thermal shields to minimize the reflections. Data acquisition component 42A also can perform one or more image analysis techniques, such as image thresholding, to separate strong sources of infrared radiation from weaker reflections. Additionally, data acquisition component 42A can process multiple near-identical infrared images, e.g., those captured by a high speed infrared imaging device 22, to combine the infrared image data to eliminate noise, frame artifacts, blurs from insects, dirt, or the like. Furthermore, data acquisition component 42A can process the multiple near-identical infrared images to increase an overall resolution, thereby enabling the detection of more subtle details, e.g., using typical image fusion, image filtering, super-resolution, image interpolation, and/or the like.

Figure 5A:
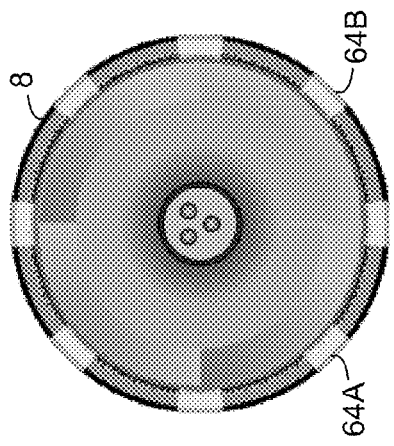
FIGS. 5A-5D show illustrative conceptual infrared patterns that can be imaged for rail wheels according to an embodiment.
Figure 5B:
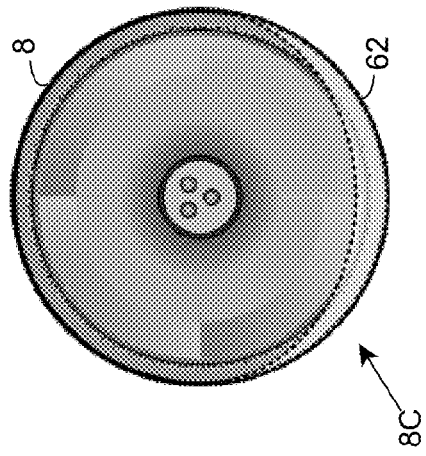

FIGS. 5A-5D show illustrative conceptual infrared patterns that can be imaged for rail wheels according to an embodiment. In FIG. 5A, an infrared pattern is shown for a rail wheel 8 that has been standing in the sunshine for a period of time. In this case, the sunshine has shone on the lower portion 8C of wheel 8 (due to shadows cast by other portions of the rail vehicle) forming a corresponding crescent-shaped area of heating 62. In an embodiment, advanced analysis component 42C can identify such a pattern and prevent it from triggering an alert. In FIG. 5B, an infrared pattern is shown for a rail wheel 8 that is chattering, e.g., repeatedly rotating and stopping, during the forward motion of the rail vehicle. In this case, wheel 8 includes numerous patches, such as patches 64A, 64B, of significant heating around its perimeter, corresponding to locations of the wheel 8 that have stopped and therefore rubbed against the rail rather than rolling freely. In an embodiment, advanced analysis component 42C can identify such a pattern and trigger a corresponding alert indicating the flaw.

Figure 5C:
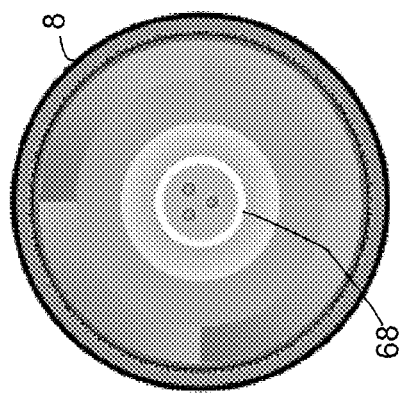
Figure 5D:
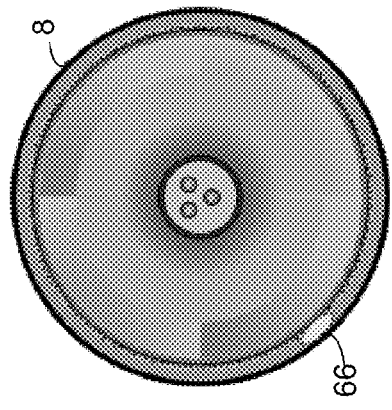

In FIG. 5C, an infrared pattern is shown for a rail wheel 8 having a single flat spot, e.g., due to a previous incident of locked brakes. In this case, wheel 8 includes a single patch 66 of significant heating, which corresponds to additional friction created each time the flat spot contacts the rail. In an embodiment, advanced analysis component 42C can identify such a pattern and trigger a corresponding alert indicating the flaw. In FIG. 5D, an infrared pattern is shown for a rail wheel 8 that exhibits no direct anomalies, but which includes evidence of overheating of the hub and bearing. In particular, wheel 8 includes a bright area 68 in the central portion of the wheel that attaches to the hub and bearing. In an embodiment, advanced analysis component 42C can identify such a pattern and trigger a corresponding alert indicating the flaw.

Infrared image-based analysis of one or more components of a rail vehicle 4 can utilize a three-dimensional temperature map of the component, such as a rail wheel 8. Three-dimensional analysis enables topological processes to be applied to the analysis of the image data, which can provide a significant advantage when analyzing images including three-dimensional objects with certain characteristics. To this extent, an embodiment of analysis component 42B (FIG. 3) can generate three-dimensional temperature maps based on the infrared image data acquired for one or more components of a rail vehicle 4.

Figure 6:
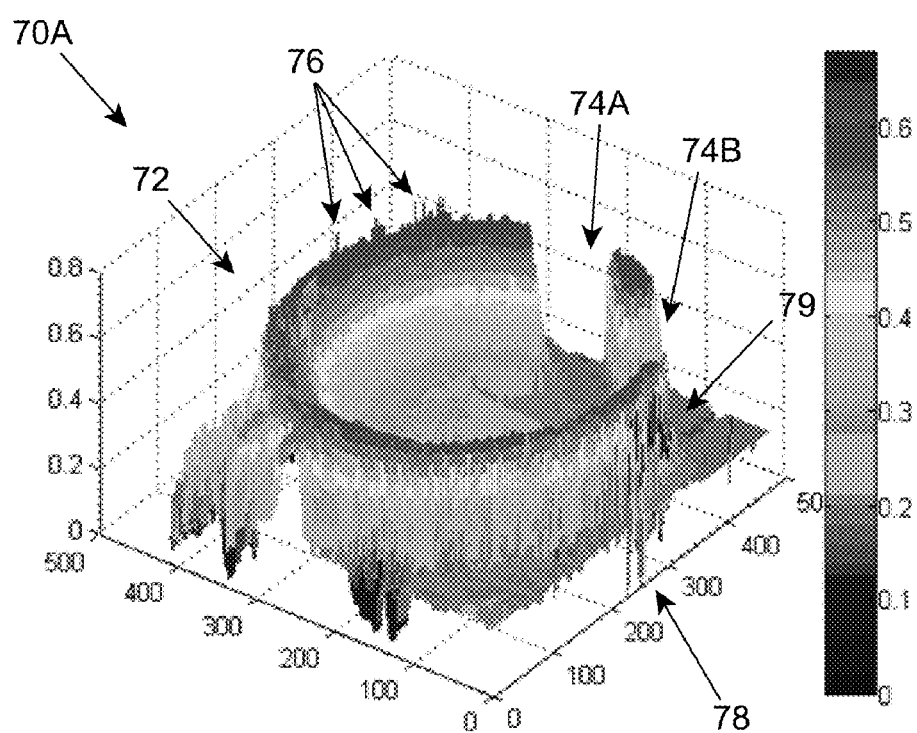
FIG. 6 shows an illustrative pair of three-dimensional temperature maps for a hot rail wheel according to an embodiment.
Figure 6:
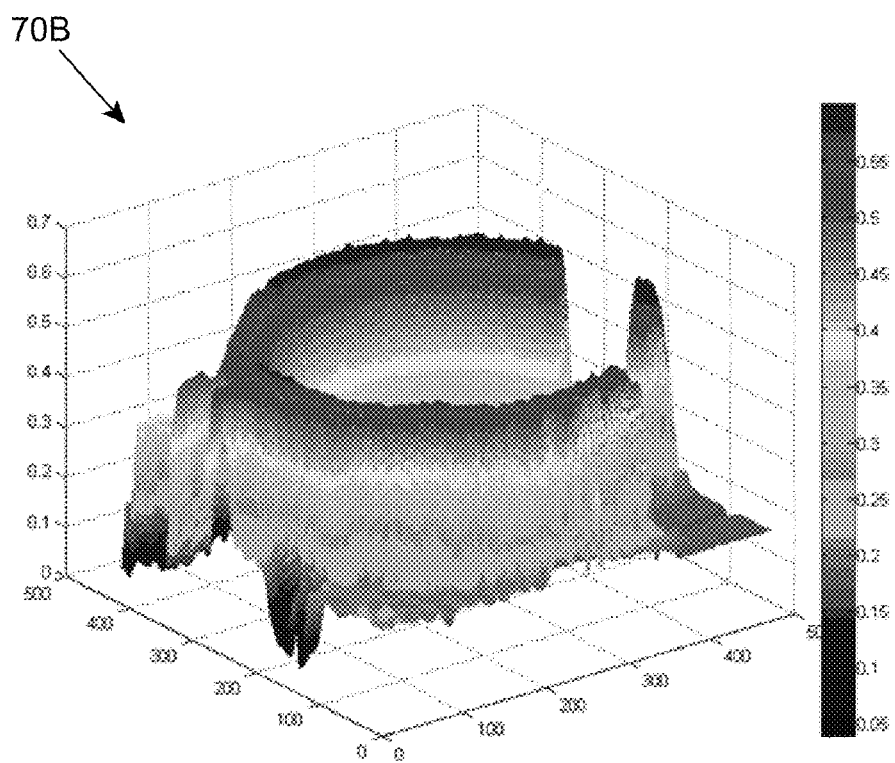

For example, FIG. 6 shows an illustrative pair of three-dimensional temperature maps 70A, 70B for a hot rail wheel, which can be generated by analysis component 42B, according to an embodiment. Temperature map 70A comprises a temperature map of the raw infrared image data converted into the three-dimensional view. As illustrated, the rail wheel is visible as a raised area 72 above the background temperature level of the image. However, gaps 74A, 74B are clearly present, as well as noise in the image. For example, there are high temperature spikes 76, low temperature spikes 78, which can have a significant effect on the overall outline. Additionally, there is an area 79 of significantly lower temperature visible on what apparently should be a much warmer area of the wheel. There are a number of causes of such noise, both internal (e.g., electronic noise present in the sensor or accompanying electronics, etc.) and external (e.g., reception of errant RF signals by electronic circuits, reflections from wheel surface, etc.). Such temperature spikes are responsible for both false positive and false negative readings in single-point sensor solutions.

Acquisition subsystem 12 (FIG. 3) and/or analysis component 42B can implement any combination of various physical and/or electronic processes to reduce or remove noise from the infrared data. For example, analysis component 42B can apply a Gaussian noise filter to temperature map 70A to generate temperature map 70B. As illustrated, the raised area 72 corresponding to the rail wheel is much smoother and more consistent in outline. Moreover, all of the spurious temperature spikes 76, 78 are reduced or removed, and the area 79 of lower temperature is much more in line with the temperatures of the surrounding areas.

Advanced analysis component 42C (FIG. 3) can analyze the three-dimensional maps 70A, 70B using any combination of various processes that directly take into account the physical nature of the target object, such as a rail wheel. For example, advanced analysis component 42C can locate the target object(s) of interest (e.g., rail wheels and associated hardware) using a geometric fit of a circle (or appropriately deformed circle, depending on the angle of view) of a roughly correct size to infrared and/or visible image data. As the acquisition subsystem 12 will be installed with a known angle and distance to the set of tracks, the distances of the target objects, such as rail wheels, will be very heavily constrained. Additionally, variance in size will be relatively small compared to, for example, the difference in size between the wheels of a compact car and those of a large truck.

Similarly, advanced analysis component 42C can perform analysis of the image while taking into account realities of physical phenomena. For example, the heat distribution of solid objects is generally even and symmetrically decreasing with distance from the heat source. Discontinuities in the heat distribution can indicate discontinuities in the physical object. However, large discontinuities, such as 74A, 74B, can be indicative of an object blocking the ability of the imaging device to acquire infrared data for the target object. Advanced analysis component 42C can utilize additional knowledge of the expected configuration of the components of rail vehicles to identify the blocking object as a portion of the support section of the truck.

Regardless, advanced analysis component 42C can analyze the height of the raised portion 72 for consistency of height, slope in three dimensions, and other parameters, which can provide considerable information regarding the imaged rail wheel. For example, advanced analysis component 42C can determine which locations, if any, on the rail wheel may be hot, and compare these locations with the structure of the wheel and related components to determine the actual condition that may be present.

An embodiment of analysis component 42B (FIG. 3) can generate a set of wavelet transforms based on the infrared image data and/or other data, such as acoustic data, acquired by acquisition subsystem 12 (FIG. 3). Wavelet transforms separate image data and other signals, such as acoustic signals, into high and low frequency components. By selecting the correct level of decomposition, the wavelet transform often enables analysis to identify key features of the image data or signal which were not readily identifiable within the original signal.

Figure 7A:
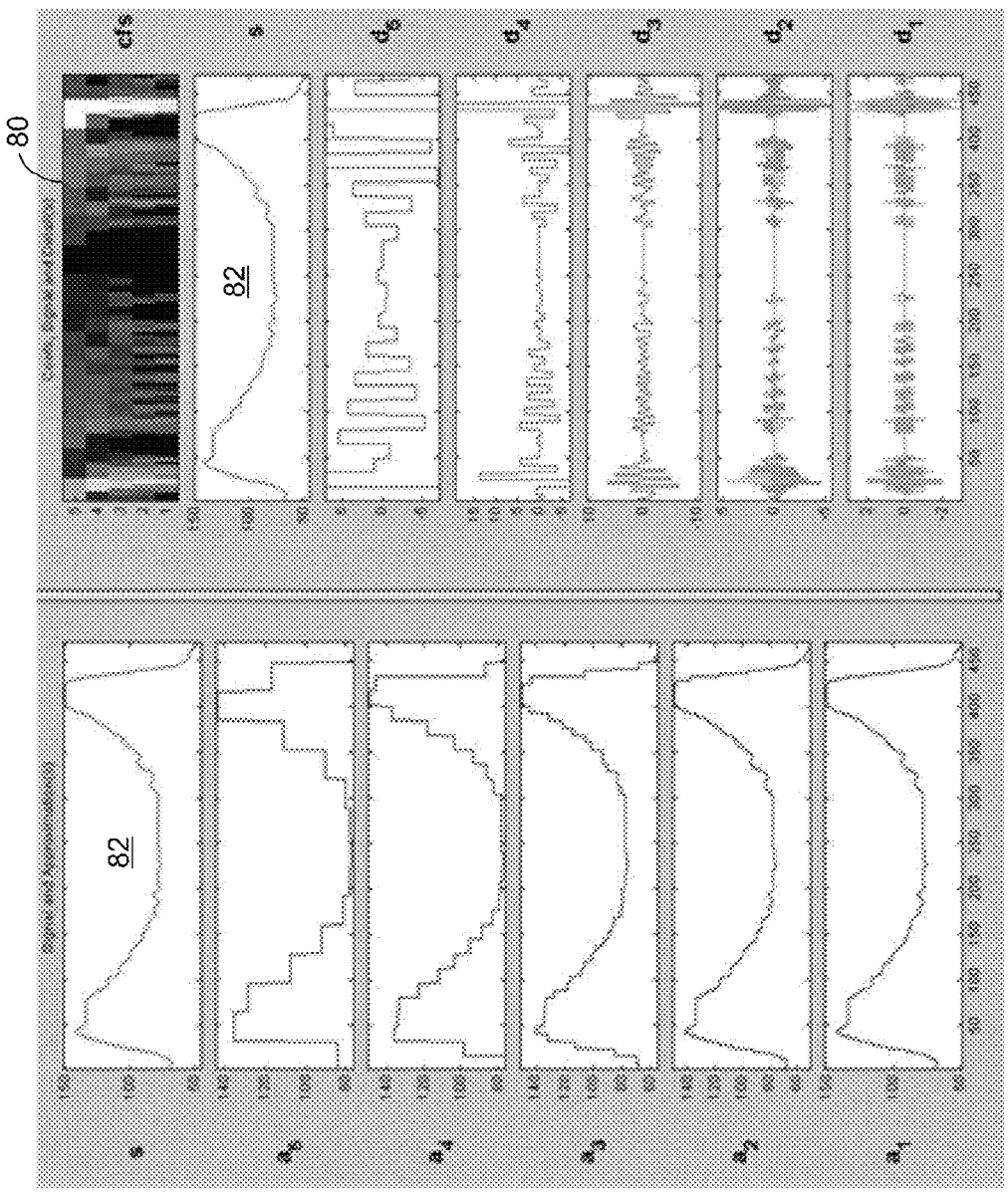
FIGS. 7A, 7B show illustrative applications of wavelet transforms on infrared image data for a rail wheel according to an embodiment.
Figure 7B:
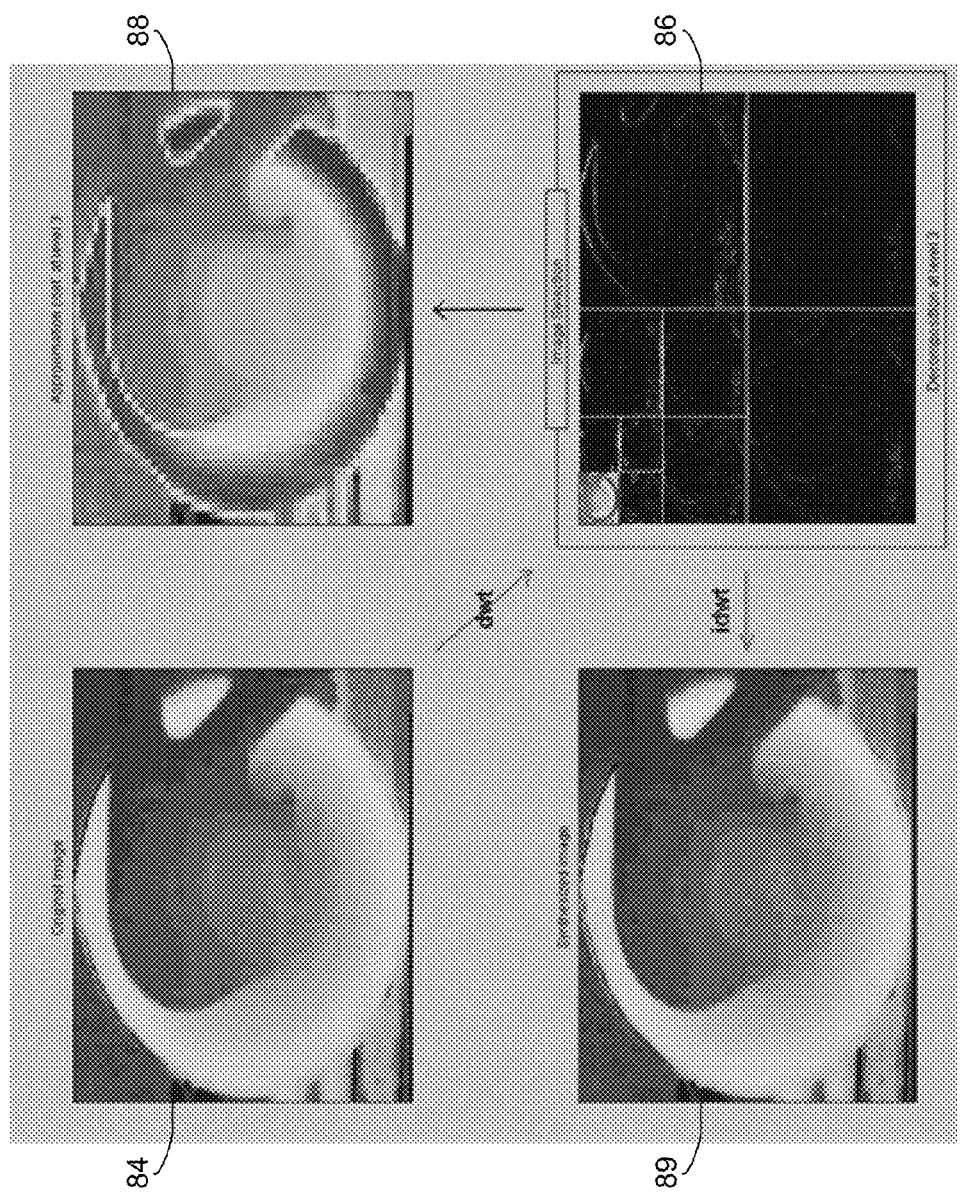

For example, FIGS. 7A, 7B show illustrative applications of wavelet transforms on infrared image data for a rail wheel, which can be generated by analysis component 42B, according to an embodiment. In FIG. 7A, a two-dimensional plot 80 of the heat distribution measured across a particular rail wheel (cfs) is shown. As illustrated, the plot is not a smooth distribution, but includes a number of light and dark areas. Analysis component 42B can generate a primary representation of the two-dimensional plot 80 as a single function (s) 82. Analysis component 42B can decompose this representation into a number of decomposition levels, $d_1$ through $d_5$, each of which analysis component 42B can re-translate into a single graphical function, $a_1$ through $a_5$, respectively. As illustrated, varying levels of detail are represented by the different levels of decomposition.

FIG. 7B shows an application of wavelet transform on an infrared image for a rail wheel, which brings out a feature that would be much more difficult to extract from the base image. In particular, analysis component 42B can decompose an original infrared image 84 down three levels 86, and subsequently generate an approximated infrared image 88 based on the level three decomposition 86. Because the different levels of decomposition emphasize different frequency aspects of the original, the approximated infrared image 88 heavily emphasizes the temperature gradients around the rail wheel. As a result, the approximated infrared image 88 is much more amenable to standard image processing (edge detection, etc.) than the original infrared image 84, whose color differentials in that region would tend to blur the edges and make defining the actual areas of temperature increase difficult. Analysis component 42C can use the various levels of decomposition to generate a reconstructed infrared image 89, e.g., to verify the validity of the wavelet decomposition. As illustrated, reconstructed infrared image 89 is substantially identical to the original infrared image 84, thereby verifying the validity of the wavelet decomposition.

As described herein, various conditions can be detected by system 10 (FIG. 3), and various responses can be initiated/performed in response to a detected condition. Several of these conditions cannot be detected by previous approaches. For example, system 10 can determine when a bearing 6C (FIG. 1B) may be failing. Under normal operation, the bearing 6C rarely varies more than a very few degrees from ambient temperature. At high speeds, a failing bearing 6C can become extremely hot causing heating in the axle area. Even at low speeds, the dissipation of energy from such a massive vehicle can heat up a failing bearing 6C by approximately ten degrees F., which is too small of a variation for prior art approaches to detect.

Additionally, system 10 can detect brake failures. During normal operation, brakes that are applied evenly across an entire train would be expected to heat the wheels (for drum-style tread brakes) or discs (for rotary disc brakes) to roughly the same degree on all rail vehicles. System 10 can detect the presence of a significant temperature variation (e.g., greater than approximately five degrees F.) between the braking system and/or corresponding rail wheel of rail vehicles, and identify such a difference as an indication of brake failure. Brake failure modes generally are of two classes: failure of the brake to engage when needed, and failure of the brake to release when not needed. The latter will cause wheels/discs to become significantly hotter than their neighbors, while the former would cause them to be significantly cooler. Additionally, the brake failure can be for a single rail wheel, in which case system 10 can identify the single location as exceeding a tolerable variation, or an entire rail vehicle, in which case system 10 can identify the braking system for the entire rail vehicle as exceeding a tolerable variation.

System 10 can detect various other conditions. For example, a stuck rail wheel 6 (e.g., due to a locked bearing or brake) can be detected by a lack of co-rotation with the motion of the rail vehicle and/or by a heated location at the wheel-rail interface. System 10 also can detect wheel chattering by identifying co-rotation out of step with other rail wheels and not equivalent in the distance of lateral motion of the rail vehicle and/or heated spots around the tread wherever the sticking is taking place. Additionally, system 10 can detect truck misalignment, which can cause asymmetrical heating of the wheels on one rail vehicle when compared with others. Furthermore, system 10 can detect flat spots and out of round conditions of a wheel, which cause hotter spots on the tread surface of the wheel.

System 10 also can detect a flaw in a rail wheel (e.g., crack, internal flaw) using the infrared image data according to an embodiment. In particular, system 10 can acquire infrared image data for a rail wheel at least once before and at least once after heating. For example, system 10 can acquire infrared image data for a rail wheel on an approach to a hill and near the bottom of the hill (after significant braking would have heated the wheels). Alternatively, system 10 can include a heat source, such as a flash lamp, combustion-based heater, inductive heating mechanism, and/or the like, which applies heat to the rail wheel. System 10 can acquire infrared image data in multiple locations after the wheel is subjected to heating to further analyze the wheel as it cools.

Regardless, analysis subsystem 30 (FIG. 3) can perform thermographic analysis of the wheel to detect one or more features of the object, such as a subsurface flaw. To this extent, analysis subsystem 30 can apply a set of active thermography algorithms to locate flaws and determine their sizes/severity from the infrared image data. These algorithms can include but are not limited to: modeling the permeation of heat through a standard wheel and comparing actual heat profiles with an idealized profile and/or with file profiles of known flawed wheels; computing temperature gradients and determining coordinates of the largest gradient points; performing FFT transformation of the infrared image sequences to analyze frequency over the temperature evolution; wavelet analysis to enhance features; and/or the like.

Figure 8:
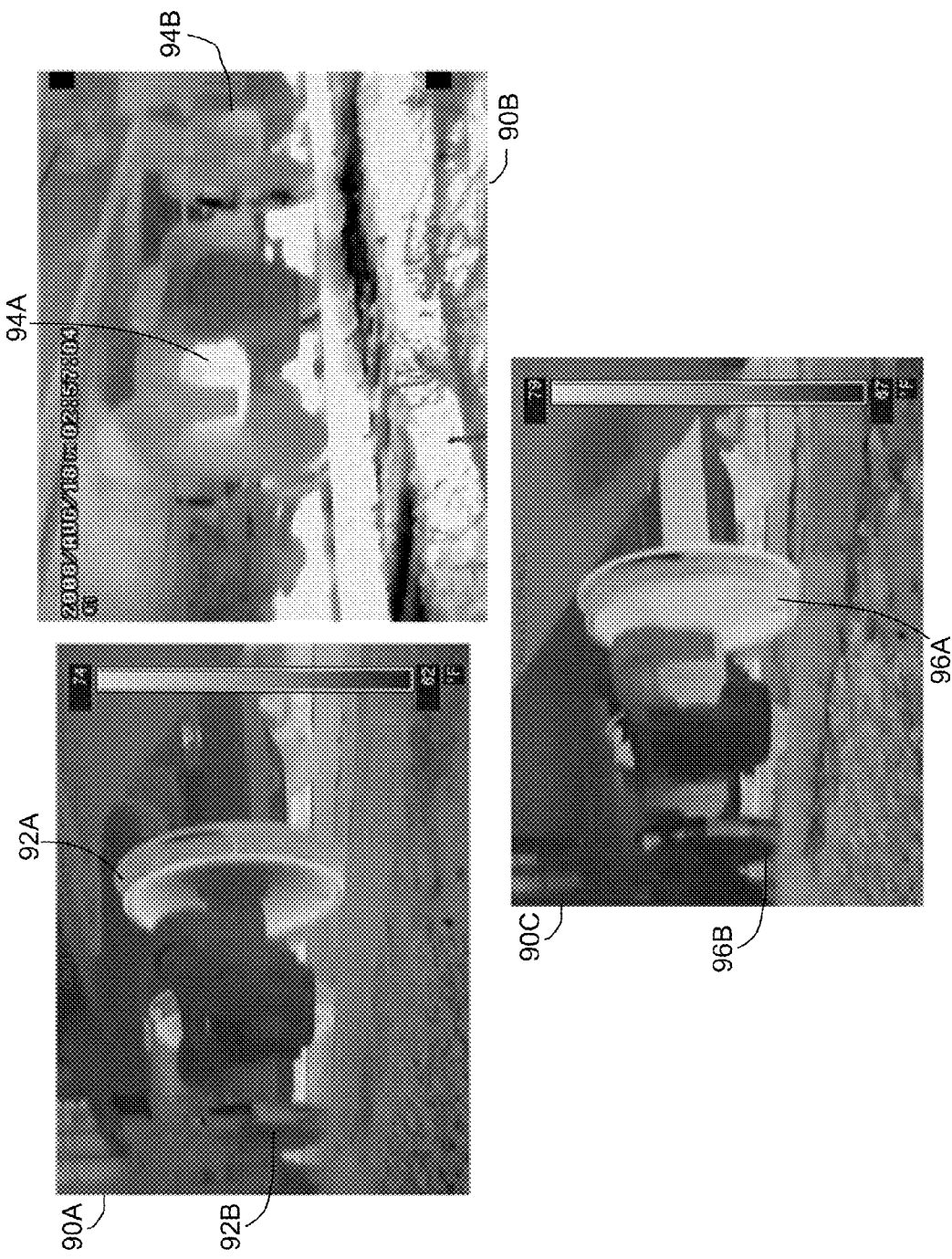
FIG. 8 shows illustrative infrared images of rail vehicles having one or more defects according to an embodiment.

In an embodiment, system 10 detects one or more defects by comparing the temperature of a component currently being analyzed with components of the same type that are adjacent (e.g., on the same vehicle) or have been recently analyzed (e.g., on a recently imaged vehicle). When a sufficient difference is noted between one component and other comparable components, system 10 can identify the component as including a defect. FIG. 8 shows illustrative infrared images 90A-90C of rail vehicles having one or more of these defects according to an embodiment. In image 90A, rail wheel 92A is substantially brighter than its neighboring rail wheels, such as rail wheel 92B, which is indicative of a stuck brake system. In image 90B, a wheel hub bearing 94A is clearly hotter than other visible bearings 94B, which is most likely caused by poor lubrication or wear on the bearing 94A. In image 90C, the wheel, bearing, and axle of a wheel assembly 96A are significantly hotter than the corresponding components of other wheel assemblies, such as wheel assembly 96B, in the same image, which can be caused by lubrication leakage, excessive wear of bearing components, and/or the like.

In each case, system 10 can identify the temperature difference between the corresponding components and flag the anomalous component as including a defect. In general, system 10 can identify an anomalous component as a component having a temperature that is outside an acceptable range of average temperatures of corresponding components, for example, +/−two degrees F. In this manner, an embodiment of system 10 does not use absolute temperature thresholds, but rather uses relative temperature thresholds to identify defects. Additionally, based on the anomaly, system 10 can identify a particular defect that may be present. Furthermore, system 10 can use ambient information, such as a temperature of the operating environment, to identify the presence of a defect. For example, system 10 can identify a wheel having a temperature of 0° F. when the external temperature is −20° F. as overheated, while a wheel having a temperature of 80° F. when the external temperature is 100° F. can be identified as under-heated.

In an illustrative implementation, system 10 (FIG. 3) is integrated into the processing of rail vehicles in a classification yard (e.g., hump yard). Rail wheels 8 and other components of rail vehicles 4, include sufficient thermal mass to retain heat for a significant period of time after operation. To this extent, even when not operating at a relatively high speed, differences in temperatures between a component having a defect and other components operating properly can be detected by system 10. Additionally, by using relative differences instead of fixed temperature thresholds, system 10 can identify components that stand out from other components due to abnormal heating, which may be caused by a flaw/condition.

Figure 9:
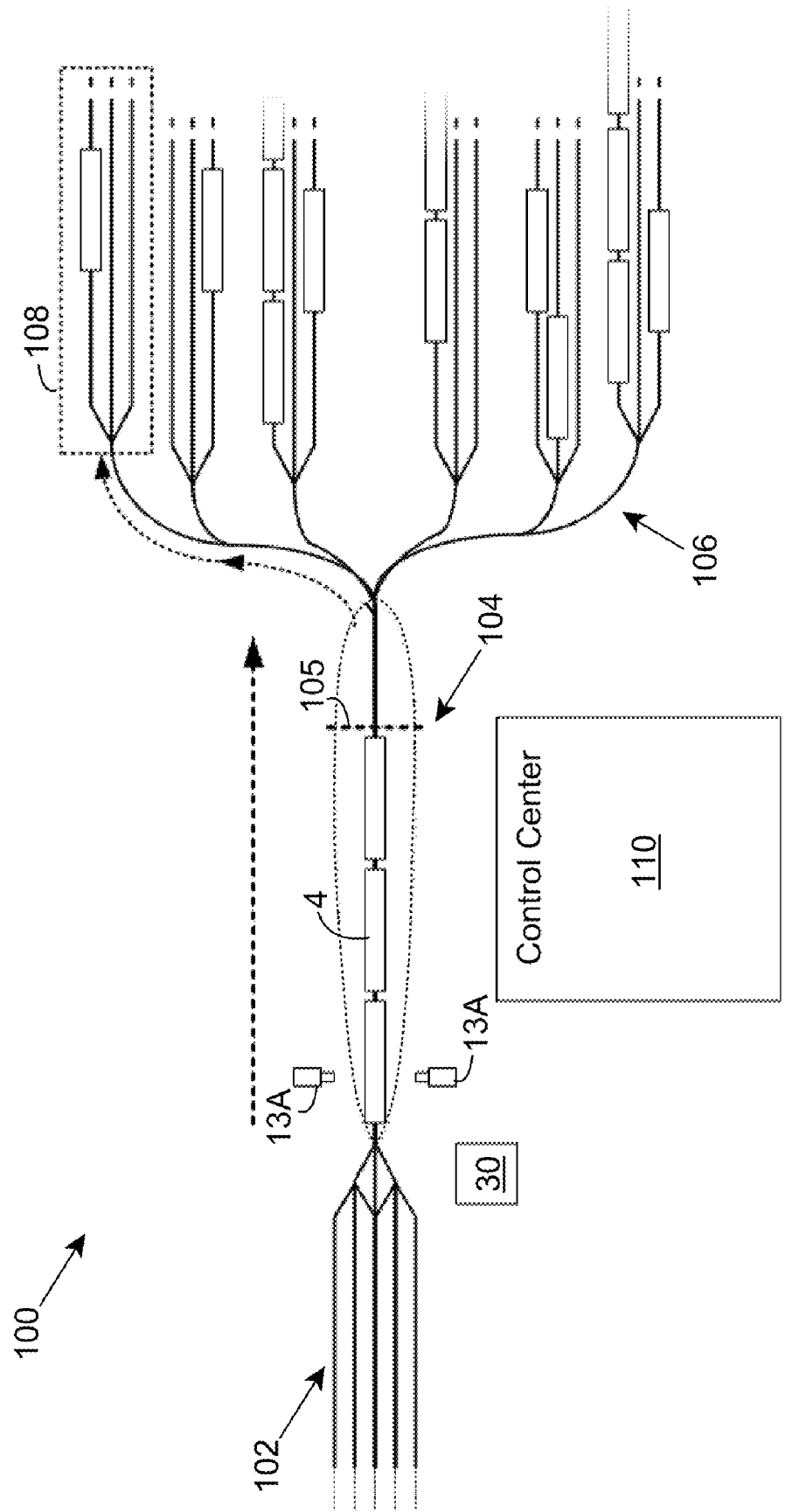
FIG. 9 shows a simplified diagram of an illustrative classification yard according to an embodiment.

FIG. 9 shows a simplified diagram of an illustrative classification yard 100 according to an embodiment. In general, classification yard 100 includes a set of incoming tracks 102 that receive incoming trains. Tracks 102 feed into a single line 104, which includes a "hump" causing the rail vehicles to go up an incline and then down. After passing the crest 105 of the hump, rail vehicles 4 roll into a bowl area 106 and are directed to a particular track in the bowl area 106 by a control center 110. If a rail vehicle 4 is determined to have a defect, control center 110 can route the rail vehicle 4 to a set of repair/maintenance tracks 108. In general, an individual decouples certain rail vehicles 4 from one another at or before the crest 105 of the hump based on directions received from the control center 110 to route the rail vehicles 4 different tracks in the bowl area 106 or repair maintenance tracks 108.

In an embodiment, classification yard 100 is modified to include system 10 (FIG. 3). In particular, a set of instrumentation emplacements 13A, 13B for acquisition subsystem 12 (FIG. 3), each of which is configured to acquire vehicle data 50, including infrared image data for one or more components of the rail vehicles 4 (e.g., rail wheels), as they move along line 104, are located adjacent to line 104. Additionally, analysis subsystem 30 is incorporated in classification yard 100 to perform thermal imaging-based rail vehicle analysis as described herein. Analysis subsystem 30 can communicate the results of the analysis to control center 36, which can adjust the rail vehicle routing, if necessary, to address any faults/conditions identified by analysis subsystem 30.

Implementation of system 10 at a classification yard, provides several advantages over installations on a mainline. For example, by imaging the rail vehicles 4 at slower speeds (e.g., twenty miles per hour or less), infrared imaging devices 22 (FIG. 3) capable of imaging at approximately thirty frames per second can be utilized. Speeds in a typical classification yard 100 rarely exceed ten to fifteen miles per hour. Additionally, the infrared image data is captured shortly after the train underwent braking to slow down for the classification yard 100, which will enable a better analysis of faults that may be present in the braking system. Further, the classification yard often includes repair tracks 108, which can be used to immediately route a rail vehicle 4 for repair. On a mainline, the rail vehicle 4 will often need to keep going until reaching the destination.

System 10 also can determine whether a rail vehicle 4 having a dragging brake/wheels will be able to complete coupling or travel sufficiently far into the bowl area 106 before the rail vehicle 4 has reached the crest 105 of the hump. In this manner, control system 110 can adjust operation of retarders or the like, to enable the rail vehicle 4 to travel sufficiently far, re-route the rail vehicle 4, if necessary, and/or the like. Additionally, a set of instrumentation emplacements 13A, 13B can be located after the crest 105 of the hump. In this case, the infrared image data can provide information on an ability of the rail vehicle 4 to couple. For example, if the brakes of the rail vehicle 4 are dragging, the retarders on the hump may slow the rail vehicle 4 too much so that no coupling will occur with another rail vehicle 4 located in the bowl area 106. Still further, a set of instrumentation emplacements 13A, 13B can be located at the point of decoupling. In this case, analysis subsystem 30 can analyze the infrared image data to detect any brake problems, such as a leak that occurs after the decoupling.

While system 10 is described as being implemented at a line 104 of a classification yard 100, it is understood that embodiments of instrumentation emplacements 13A, 13B can be implemented anywhere within classification yard 100. Additionally, it is understood that system 10 can be implemented anywhere within the rail environment, including on a mainline. In a mainline implementation, system 10 can include higher-speed imaging devices capable of operating at 1000 fps or even higher speed to acquire clear image data of rail vehicle components moving at speeds up to 250 miles per hour or more. Regardless, system 10 can perform similar analysis of the wheels, brakes, and/or the like, as described herein. When a flaw/condition is detected, system 10 can remotely communicate with a control center 110 of a classification yard 100, which can prepare for a subsequent arrival and processing of the train accordingly.

When implemented on a mainline, a location can be selected in which sets of instrumentation emplacements 13 (FIG. 1B) are located before and after a hill. In this case, a rail vehicle having brake or related problems can be more readily identified since the brakes will not be in use going up the hill, but will be going down. Additionally, the train may not be traveling as fast, making the components easier to image and track.

Various approaches can be implemented to ensure that detailed infrared image data can be acquired for a rail vehicle regardless of its speed. For example, the speed of image acquisition of an infrared imaging device can be significantly increased from thirty fps to hundreds of frames per second by selecting a particular ROI (Region of Interest) to be imaged, rather than acquiring image data for the entire field of view. Additionally, as discussed herein, fusion with lower-resolution infrared image data acquired with a faster infrared imaging device with higher resolution visible image data can enable continued determination of many of the conditions of interest without adversely affecting performance of the system. Still further, infrared image data can be acquired by one-dimensional linear arrays properly synchronized with the speed of the rail vehicle to create two-dimensional images. Many linear arrays have readout times sufficiently faster than two-dimensional imaging devices so that the use of a linear array in this fashion can permit much higher rate infrared imaging of passing vehicles.

As discussed herein, embodiments of system 10 provide significant advantages over alternative approaches that utilize minimal point sensors and lower sensitivity sensors. For example, an embodiment of system 10 can provide improved safeguards against costly false positives through the use of: higher resolution image data, which enables differentiation between sources of heat; statistical analysis and/or image filters to eliminate false positives caused by a few anomalous point readings (e.g., due to noise, malfunctioning pixel, reflection, and/or the like); multi-frame image processing to reduce false positives (e.g., detect and eliminate dead or malfunctioning pixel(s) from analysis); and/or the like.

A significant problem with prior art approaches is sensor saturation, which can occur due to local heating, sunlight, or another heat source, which causes the sensor to essentially see nothing. System 10 can implement various infrared imaging approaches to automatically determine whether the sensor is actually detecting a tremendous heat source or whether it is simply oversensitive for current conditions, and adjust that sensitivity. For example, in one embodiment, system 10 generates and analyzes an image histogram that plots the frequency of intensities found across the image. A "good" image will generally have a reasonably "bell-shaped" curve, showing that most of the image is in the midrange intensity areas but that there is a good distribution of intensities from bright to dark; a saturated image will have a severely distorted curve heavily biased towards the bright end, showing that most of the image is extremely bright, perhaps essentially white, and thus lacking detail which would be visible if the "glare" were reduced. System 10 can further attempt to reduce the glare by performing histogram equalization and/or other contrast/brightness adjustments, adjusting the sensitivity of the infrared imaging device, and/or the like.

As discussed herein, acquisition subsystem 12 (FIG. 3) can comprise a wide-angle infrared imaging device 22 (FIG. 3), which is configured to capture an image substantially perpendicular to a set of tracks. In this case, despite the image having a substantially perpendicular field of view, various components of a rail vehicle that are located under the rail vehicle and/or on the opposite side of the rail vehicle can be imaged. A standard infrared imaging device 22 comprises an angular field of view of approximately 40-60 degrees. In an embodiment, infrared imaging device 22 comprises an angular field of view in excess of sixty degrees, e.g., approximately 120 degrees.

Figure 10:
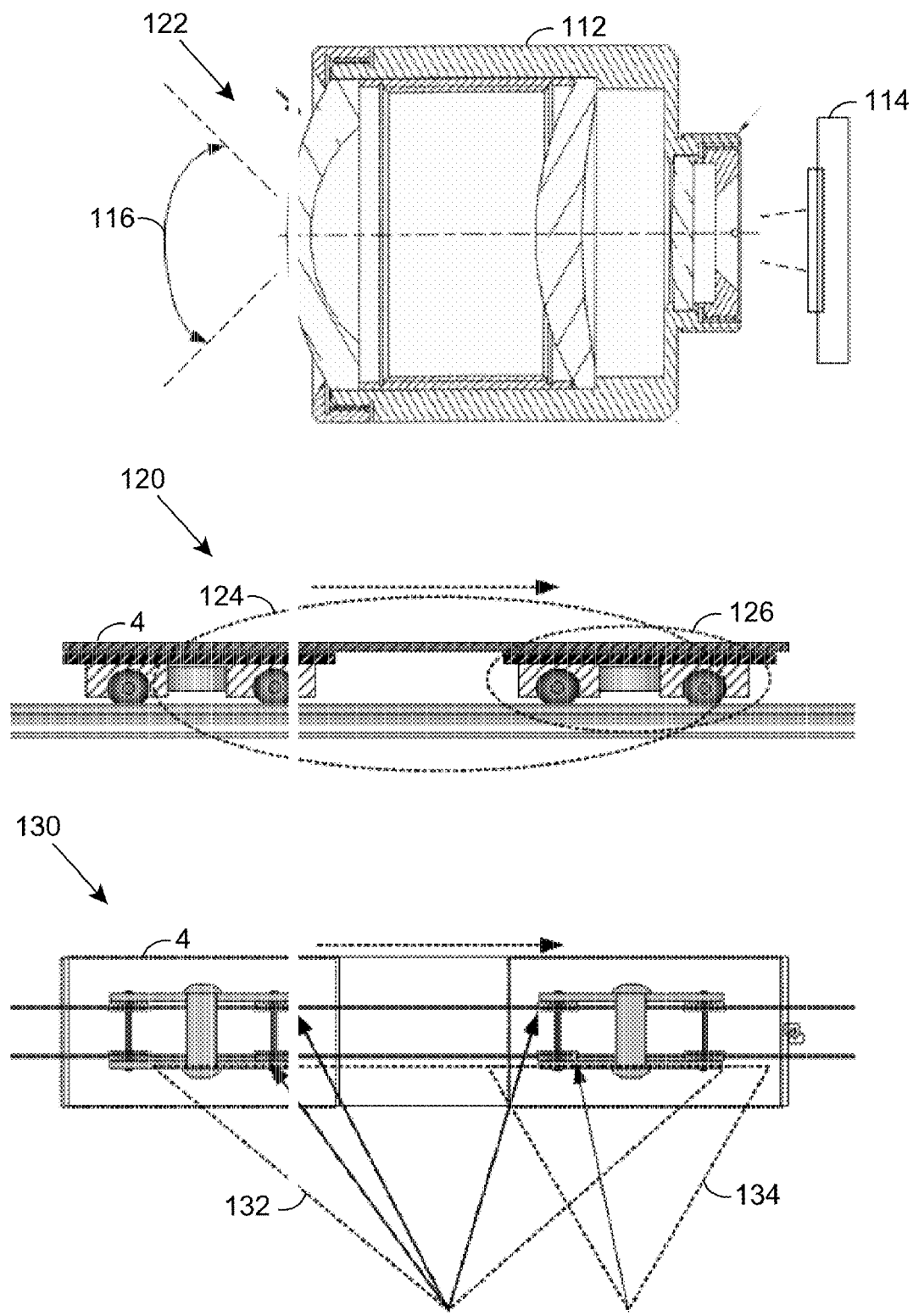
FIG. 10 shows illustrative use of a wide-angle infrared imaging device according to an embodiment.

To this extent, FIG. 10 shows illustrative use of a wide-angle infrared imaging device 122 according to an embodiment. Device 122 includes a wide-angle infrared imaging lens 112, which can include optical elements transparent to infrared radiation (e.g., germanium). Lens 112 projects images onto an infrared imaging array 114 and has an angular field of view 116 of approximately 120 degrees. As illustrated by a side view 120 of an illustrative rail vehicle 4 imaged using the wide-angle infrared imaging device 122, the imaged area 124 can include image data for multiple wheel trucks, while the imaged area 126 of a narrower (e.g., 60 degree) field of view can only include a single wheel truck. In this case, analysis subsystem 30 (FIG. 3) can perform a direct comparison between the relative heat signatures of two adjacent wheel trucks using a single infrared image having the imaged area 124.

Additionally, as illustrated by a top view 130 of an illustrative rail vehicle 4 imaged using the wide-angle infrared imaging device 122, the wide angle view 132 can be configured to include clear lines of sight to rail wheels on both sides of the rail vehicle 4. By contrast, a narrower field of view 134 does not provide as good of a line of sight when capturing an image of the entire wheel truck.

Figure 11:
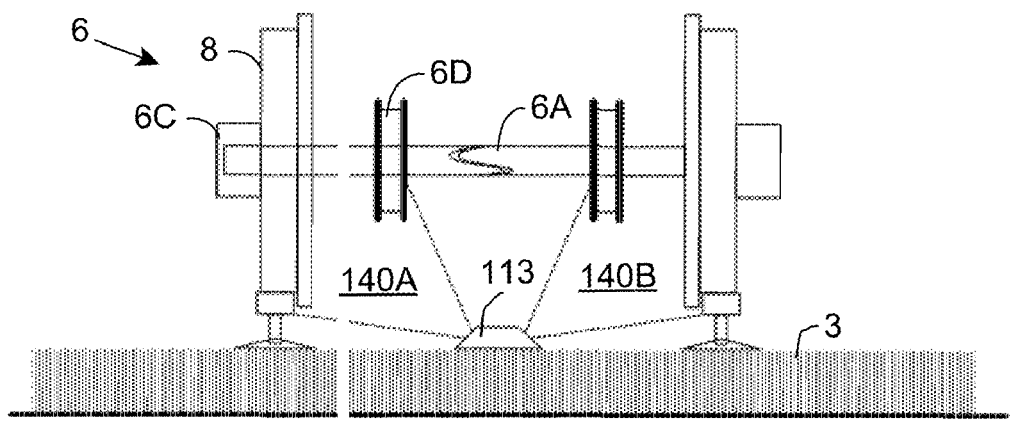
FIG. 11 shows an alternative instrumentation emplacement according to an embodiment.
Figure 11:
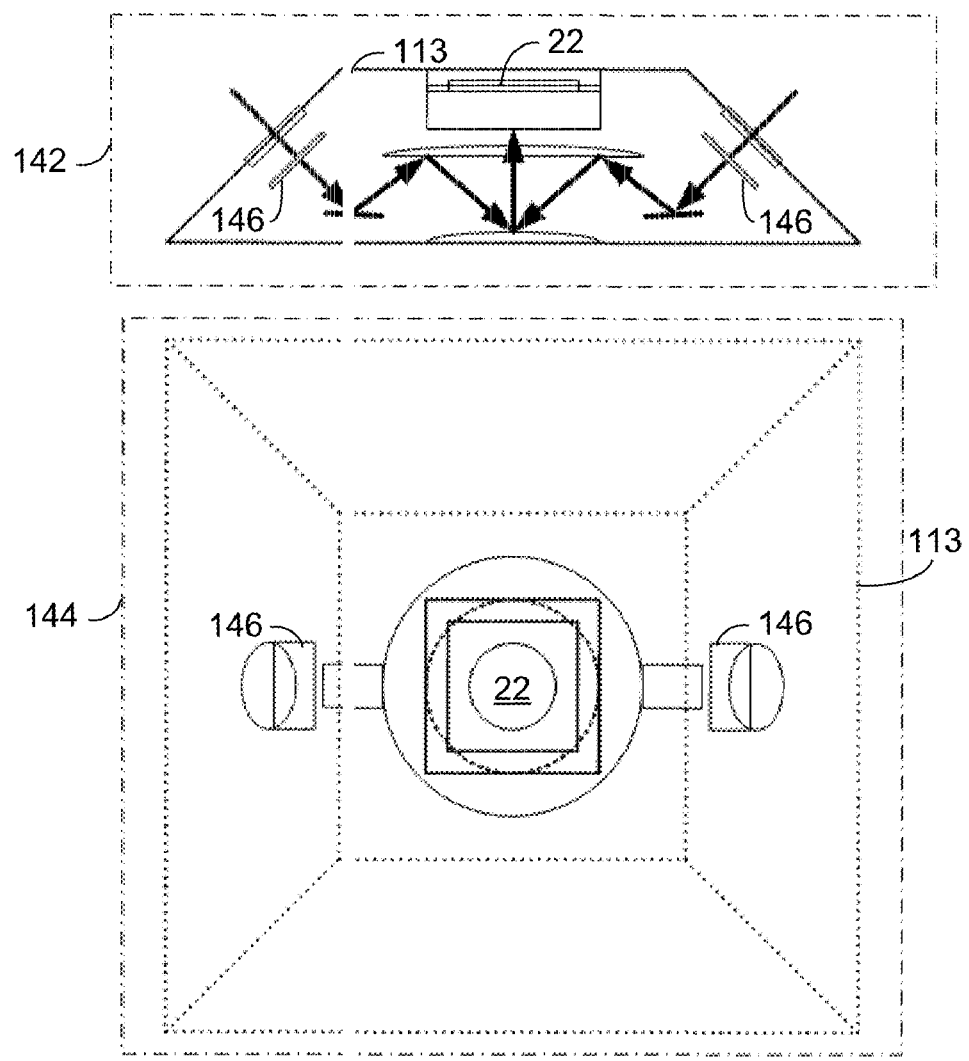

While primarily shown and described as utilizing a set of instrumentation emplacements 13 (FIG. 1B) located outside and adjacent to a set of tracks, it is understood that an embodiment of the invention can utilize a single instrumentation emplacement and imaging device to acquire complete image data for the left side wheel, right side wheel, bearings, brakes, disk brakes, and other vehicle components. To this extent, FIG. 11 shows an alternative instrumentation emplacement 113, which is configured to be installed between a pair of rails, according to an embodiment. Instrumentation emplacement 113 can be temporarily or permanently placed on or embedded in the ground/ballast 3 between the rails, and have fields of view 140A, 140B such that when a wheel assembly 6 passes, the instrumentation emplacement 113 can image the wheels 8, brake disc 6D, shaft 6A, the rear of bearing assembly 6C, etc.

Instrumentation emplacement 113 can acquire infrared image data for the fields of view 140A, 140B using two or more imaging devices 22 (FIG. 3). In an embodiment, instrumentation emplacement 113 acquires the infrared image data for fields of view 140A, 1408 using a single infrared imaging device 22. For example, instrumentation emplacement 113 can implement a solution for acquiring image data from multiple directions as shown and described in U.S. Pat. No. 7,298,548, which is hereby incorporated by reference. In this case, as illustrated in the side cutaway view 142 and top view 144 of instrumentation emplacement 113, instrumentation emplacement 113 includes a single infrared imaging device 22. As illustrated by the arrows, infrared radiation from both fields of view 140A, 140B enters through a lens/window and is reflected using a set of mirrors onto the infrared imaging device 22.

To permit clear acquisition of both fields of view, instrumentation emplacement 113 can include electronic shutters 146, which alternate being open and closed at a speed commensurate with the frame rate of the infrared imaging device 22. In this case, each field of view is imaged every second frame, with the other field of view being imaged in the alternate frames. However, when the resolution of the infrared imaging device 22 is sufficient, instrumentation emplacement 113 can be configured such that infrared radiation from both fields of view 140A, 140B is directed onto unique portions of the infrared imaging device 22, thereby enabling imaging device 22 to simultaneously image both fields of view 140A, 140B. It is understood that embodiments of instrumentation emplacement 113 may comprise other components, such as shutters to open and close viewing ports for protection, additional imaging devices for multispectral data acquisition, acoustic sensors, and/or the like.

As discussed herein, acquisition subsystem 12 (FIG. 3) can include a sensor 25 (FIG. 3) for acquiring non-image data of a passing rail vehicle, such as acoustic data. Analysis subsystem 30 (FIG. 3) can include an expert system, neural network, Bayesian network, and/or the like, which can identify the acoustic signature of a flaw/condition (e.g., the sticking of a wheel or brake, presence of a flat spot, or the like), and localize the acoustic signal for co-registration with the image data for the rail vehicle. By combining these acoustic signal results with the infrared image data, analysis subsystem 30 can produce greater confidence in the detection of various flaws, and can determine unique infrared signatures for flaws normally detected only by acoustic sound or direct inspection.

In transit rail vehicles systems, the same rail vehicles often travel the same routes on a regular basis as part of trains that include far fewer rail vehicles than freight trains. A transit train will typically include the same rail vehicles in the same order when traveling a daily route. To this extent, when system 10 is utilized to monitor transit rail vehicles, the particular rail vehicles being inspected will be limited and generally will remain the same for an extended period of time. As a result, system 10 can be configured to perform additional monitoring functions. For example, system 10 can identify and track specific infrared image signatures for each rail vehicle. In this case, the wear and tear on individual rail vehicles and components thereof (e.g., wheels) can be observed over time. System 10 can enable predictive maintenance to be applied to a fleet of rail vehicles by determining within an acceptable margin of error when servicing will be required. For example, system 10 can build a database showing the trends of various rail vehicles over time and when they required servicing, and generate estimates based on a comparison of a rail vehicle to the trends. Since transit vehicles use disc brakes almost exclusively, acquisition subsystem 12 can include an instrumentation emplacement, such as instrumentation emplacement 113 (FIG. 11), which captured infrared image data from underneath the rail vehicle.

Figure 12:
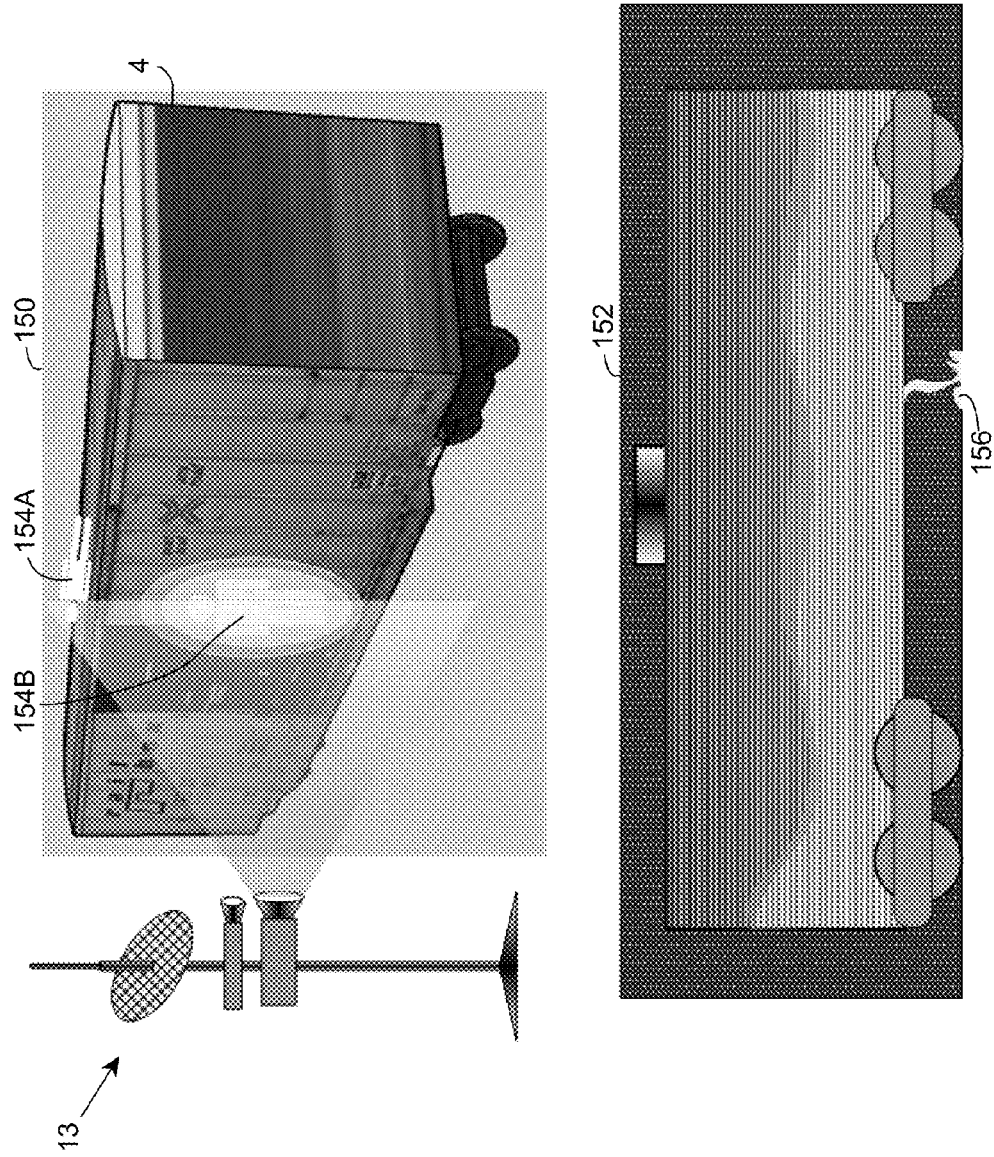
FIG. 12 shows illustrative conceptual infrared image-based security and inspection analyses, respectively, according to an embodiment.

In addition to safety/maintenance-related applications, system 10 can perform infrared image-based analysis of rail vehicles for security and inspection applications. To this extent, FIG. 12 shows illustrative conceptual infrared image-based security and inspection analyses, respectively, which can be implemented by system 10, according to an embodiment. An instrumentation emplacement 13 is shown configured to capture infrared image data 150 that includes the entire height of a rail vehicle 4 in the field of view as well as a portion of the roof. As illustrated, an outline of a person 154A, 1548 can be readily identified within the infrared image data 150. Using a sufficiently sensitive infrared imaging device, person 154B can be detected even when the doors of rail vehicle 4 are closed. This is particularly applicable for trains traveling in colder areas, which thus have a greater temperature differential between the train and any people 154A, 154B that may be present.

Similarly, instrumentation emplacement 13 can be configured to capture infrared image data 152, which includes a side view of a rail vehicle 4 that is partially filled with some cargo that is maintained at a different temperature (e.g., warmer in this case, but it could be colder) than the ambient air. In this case, the cargo is visible as a warmer portion of the rail vehicle 4 while the empty portion is visible as a darker section. The infrared image data 152 can permit system 10 to monitor a level of the cargo, determine a condition (e.g., if the cargo should be colder than ambient, but is starting to fade out from the infrared, or worse, is starting to show as warmer, there is a significant problem), and/or the like. In addition, system 10 can identify a leak 156, which would be visible in the infrared image data 152 as darker or lighter moving streams, whether it came from the cargo or from some component of the rail vehicle.

As discussed herein, acquisition subsystem 12 (FIG. 3) can acquire both infrared image data and visible image data for use in analyzing the components of a rail vehicle for the presence of any flaws. A challenge confronting any multiple camera (especially multispectral) image analysis system is registration, e.g., determining the points in the field of view of camera A that correspond directly with other points in the field of view of camera B.

FIG. 13 shows front and side views of an illustrative multi-spectral imaging device 160, for which registration can be more readily performed, according to an embodiment. Device 160 includes a first array 162 of visible light sensitive elements (each indicated by a circle), and a second array 164 of infrared sensitive elements (each indicated by a square) immediately adjacent thereto. As illustrated, each array 162, 164 can have the same resolution (e.g., be composed of the same number of elements, each of which is similar and size and orientation with respect to the corresponding paired element). However, it is understood that this does not need to be the case, as long as the two arrays 162, 164 are closely co-located and close to the same effective length in the long direction. Additionally, device 160 includes a multi-spectral lens 166, which covers both linear arrays 162, 164 and provides appropriate focus to the light and infrared radiation from the desired distance or distances of target objects. It is understood that each array 162, 164 can be equipped with a separate, single spectrum lens, instead of multi-spectral lens 166.

Regardless, since linear arrays 162, 164 are extremely small in their narrow dimension, the infrared and visible light image data acquired by the two co-located arrays 162, 164 is inherently registered to within an error proportional to the physical diameter of one of the arrays 162, 164. The error can be a very small fraction of an inch, which is an insignificant differential on the scale of most target objects, such as train wheels, and even on the scale of the expected target defects to be detected. While device 160 is shown including a single set of arrays 162, 164, it is understood that device 160 can comprise any number of sets of paired arrays 162, 164.

Regardless, during operation, device 160 simultaneously captures image data using each array 162, 164. Device 160 can be operated with appropriate timing to acquire a two-dimensional image of a moving target object. Alternatively, as discussed herein, device 160 can include a sufficient number of paired arrays 162, 164, to capture a two-dimensional image with each frame.

While shown and described herein as a method and system for analyzing components of a rail vehicle using infrared image data, it is understood that aspects of the invention further provide various alternative embodiments. For example, in one embodiment, the invention provides a method and system for analyzing any type of vehicle. For example, an embodiment can analyze: commercial vehicles such as trucks, buses, and the like, e.g., as part of a regular or random inspection, fleet management, and/or the like.

In another embodiment, the invention provides a computer program fixed in at least one computer-readable medium, which when executed, enables a computer system to analyze components of a vehicle using infrared image data. To this extent, the computer-readable medium includes program code, such as evaluation program 40 (FIG. 2), which implements some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as evaluation program 40 (FIG. 2), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for analyzing components of a vehicle using infrared image data. In this case, a computer system, such as computer system 31 (FIG. 2), can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system for analyzing a vehicle, the system comprising:
   a component configured to automatically process multi-dimensional infrared image data for the vehicle by performing a processing method including:
      identifying at least one component of the vehicle in the infrared image data; and
      determining whether any one of a set of conditions are present on the vehicle based on a relative difference between at least one of a plurality of features in the infrared image data of the at least one component and at least one of a plurality of features in infrared image data for at least one other component of the same type as the at least one component; and
   a component configured to automatically determine a set of actions in response to a determination that at least one of the set of conditions is present on the vehicle.

2. The system of claim 1, wherein the component configured to process multi-dimensional infrared image data is further configured to process multi-dimensional visible image data concurrently acquired with the infrared image data, and wherein the processing method further includes fusing the visible image data for the at least one component with the infrared image data of the at least one component, wherein the determining whether any one of a set of conditions are present uses the fused visible image data and infrared image data.

3. The system of claim 2, wherein the visible image data comprises a higher resolution than the infrared image data.

4. The system of claim 1, further comprising a component configured to acquire the multi-dimensional infrared image data for the vehicle, wherein the component configured to acquire includes:
   at least one infrared imaging device for acquiring infrared image data for the vehicle; and
   a component configured to provide the infrared image data for processing by the component configured to process.

5. The system of claim 4, further comprising:
   a known temperature source, wherein the known temperature source is within the field of view of the at least one infrared imaging device; and
   a component configured to calibrate the infrared image data based on infrared image data for the known temperature source, wherein the component configured to process processes the calibrated infrared image data.

6. The system of claim 4, wherein the at least one infrared imaging device comprises a field of view substantially perpendicular to a set of tracks on which the vehicle travels.

7. The system of claim 4, wherein the at least one infrared imaging device is configured to acquire the infrared image data as the vehicle travels over the at least one infrared imaging device.

8. The system of claim 4, further comprising at least one visible imaging device, wherein the at least one infrared imaging device includes an infrared linear array device and the at least one visible imaging device includes a visible linear array device, wherein the infrared and visible linear array devices are co-located, and wherein the infrared and visible linear array devices concurrently capture image data based on a speed of the vehicle to generate two-dimensional image data for the vehicle.

9. The system of claim 1, wherein the component configured to determine a set of actions identifies a vehicle for re-routing in response to a determination that at least one of the set of conditions is present on the vehicle.

10. The system of claim 1, wherein the infrared image data includes at least one of: infrared image data of the at least one component of the vehicle prior to an event during which the at least one component is expected to be heated or infrared image data of the at least one component of the vehicle after the event, and wherein the set of conditions include at least one of: a fault with a braking system of the vehicle or a flaw in a rail wheel.

11. The system of claim 1, wherein the determining whether any one of a set of conditions are present compares the infrared image data of a first component to infrared image data for a plurality of other components of the same type on at least one of: the vehicle or another vehicle recently imaged to determine whether at least one of the set of conditions is present.

12. A classification yard including:
   at least one infrared imaging device for acquiring multi-dimensional infrared image data for a rail vehicle in the classification yard;
   a component configured to automatically process the infrared image data for the rail vehicle by performing a processing method including:
      identifying at least one component of the rail vehicle in the infrared image data;
      determining whether any one of a set of conditions are present on the rail vehicle based on a relative difference between at least one of a plurality of features in the infrared image data of the at least one component and a plurality of features in infrared image data for at least one other component of the same type as the at least one component, wherein the at least one other component is included on at least one of: the rail vehicle, a train including the rail vehicle, or a consist including the rail vehicle;
      determining a set of actions in response to a determination that at least one of the set of conditions is present on the rail vehicle; and
      providing the set of actions for processing by a control center of the classification yard in response to the determination.

13. The classification yard of claim 12, further comprising the control center, wherein the control center re-routes the rail vehicle in the classification yard in response to a determination that at least one flaw is present on the rail vehicle.

14. The classification yard of claim 12, further comprising at least one visible imaging device for acquiring multi-dimensional visible image data for the rail vehicle concurrently with the at least one infrared imaging device, wherein the component configured to process infrared image data is further configured to process the visible image data.

15. The classification yard of claim 12, wherein the at least one infrared imaging device includes an infrared imaging device located before a location in the classification yard at which rail vehicles are decoupled.

16. The classification yard of claim 12, wherein the at least one infrared imaging device includes an infrared imaging device located after the location in the classification yard at which rail vehicles are decoupled.

17. A system for analyzing a vehicle, the system comprising:
- a component configured to automatically process multi-dimensional infrared image data for the vehicle by performing a processing method including:
  - identifying a first component of the vehicle in the infrared image data;
  - determining whether any one of a set of conditions are present on the vehicle based on the infrared image data of the first component, wherein the determining includes, for at least one condition in the set of conditions, comparing the infrared image data of the first component to at least one of a plurality of features in infrared image data for each of a plurality of other components of the same type as the first component to determine whether the at least one of the set of conditions is present; and
  - determining a set of actions in response to a determination that at least one of the set of conditions is present on the vehicle.

18. The system of claim 17, wherein the determining for the at least one of a set of conditions includes comparing at least one of a plurality of features in the infrared image data of the first component to at least one of a plurality of features in the infrared image data for each of the plurality of other components, and wherein the infrared data for the first component and the plurality of other components is acquired at a single location through which the vehicle passes.

19. The system of claim 17, wherein the infrared image data comprises a field of view substantially perpendicular to a path of travel for the vehicle.

20. The system of claim 17, wherein the infrared image data includes at least one of: infrared image data of the first component of the vehicle and the plurality of other components prior to an event during which the at least one component is expected to be heated or infrared image data of the first component of the vehicle and the plurality of other components after the event, and wherein the set of conditions includes at least one of: a fault with a braking system of the vehicle or a flaw in a rail wheel.

* * * * *